(12) United States Patent
Shaughnessy

(10) Patent No.: US 7,696,150 B2
(45) Date of Patent: Apr. 13, 2010

(54) MODULATION OF THE ACTIVITY OF AN INTERLEUKIN 17 RECEPTOR-RELATED PROTEIN, EVI27, AND USES THEREOF

(75) Inventor: John D. Shaughnessy, Little Rock, AR (US)

(73) Assignee: Board of Trustees of the University of Arkansas, Little Rock, AR (US)

( * ) Notice: Subject to any disclaimer, the term of this patent is extended or adjusted under 35 U.S.C. 154(b) by 802 days.

(21) Appl. No.: 11/128,403

(22) Filed: May 12, 2005

(65) Prior Publication Data
US 2005/0208572 A1    Sep. 22, 2005

Related U.S. Application Data

(62) Division of application No. 09/778,971, filed on Feb. 2, 2001, now Pat. No. 7,094,886.

(60) Provisional application No. 60/180,374, filed on Feb. 4, 2000.

(51) Int. Cl.
*A61K 38/00*    (2006.01)

(52) U.S. Cl. ............................ 514/2; 530/350; 530/351; 435/7.2

(58) Field of Classification Search ....................... None
See application file for complete search history.

(56) References Cited

U.S. PATENT DOCUMENTS 6,569,645 B2 *   5/2003   Chen et al. ............... 435/69.52

OTHER PUBLICATIONS

Locus Q9NRM6 (from UniPro), 2000.*

* cited by examiner

*Primary Examiner*—Dong Jiang
(74) *Attorney, Agent, or Firm*—Benjamin Aaron Adler

(57) ABSTRACT

The present invention describes the cloning and molecular and cellular characterization of a novel protein with homology to the IL-17 receptor. The gene was cloned by virtue of its proximity to a common site of retroviral integration in a murine acute myeloid leukemia. The gene described herein possibly codes for a novel interleukin receptor that binds an as yet unidentified cytokine ligand, and may be useful in cancer diagnostics and therapies that rely on immune system modulation.

5 Claims, 16 Drawing Sheets

Fig. 4

```
ILI7R    1  M G A A R S P P S A V P G P L I G L L L L L G V   25
EVI27    1                             M S L V L I S L A A   10

ILI7R   26  L A P G G A S L R L L D H R A L V C S Q P G L N C  50
EVI27   11  L C - - - - - - - - - - - R S A V P R E P T V Q C  24

ILI7R   51  T V K N S T C L D D S W I H P R N L T P S S P K D  75
EVI27   25  G S E T G P S P E - - W M L Q H D L I P G D L R D  47

ILI7R   76  L Q I Q L H F A H T Q Q G D L F P V A H I E W T L 100
EVI27   48  L R V E P V T T S V A T G D Y S I L M N V S W V L  72

ILI7R  101  Q T D A S L Y I E G A E L S V L - Q L N T N E R 125
EVI27   73  R A D A S I R L L K A T K I C V T G K S N F Q S Y  97

ILI7R  126  L C V R F E F L S K L R H H H R - - - - R W R F T 145
EVI27   98  S C V R C N Y T E A F Q T Q T R P S G G K W T F S 122

ILI7R  146  F S H F V D P D Q E Y E V T V H H L P K P I P D 170
EVI27  123  V I G E P V E L N T V V F L G A H N I P N A N M N 147

ILI7R  171  G D P N H Q S K N F L V P D C E H A R M K V T T P 195
EVI27  148  E D G P S M S V N F T S P G C L D H I M K Y K K K 172

ILI7R  196  C M S G S L W D P N I T V E T L E A H Q L R V S 220
EVI27  173  C V K A G S L W D P N I T A C K K N E E T V E V N 197

ILI7R  221  F T L W N E S T H Y Q I L L T S F P H M E N H S C 245
EVI27  198  F T T T P L G N R Y M A L I Q - - - - - - - H S T 215

ILI7R  246  F E H M H H I P A P R P E E F H Q R S N V T L T L 270
EVI27  216  I I G F S Q V F E P H Q K - K Q T R A S V V I P V 239

ILI7R  271  R N K L G C C R H Q V Q I Q P F F S S C L N D C L 295
EVI27  240  T G D S - - E G A T V Q L T P Y F P T C G S D C I 262

ILI7R  296  R H S A T V S C P E M P D T P E P I P D Y M P L W 320
EVI27  263  R H K G T V V L C P Q T G V P F P L D N N K S K P 287

ILI7R  321  V Y W F I T G I S I L L V G S V I L L I V C M T W 345
EVI27  288  G G W L P L L L L S L L V A - - - - - - - - - T W 303

ILI7R  346  R L A G P G S E K Y S D D T K Y T D G L F A A D L 370
EVI27  304  V L V A G I Y L M W R H E R I K K T S F S T T T L 328

ILI7R  371  I P P P L K P R K V W I I Y S A D H P L Y V D V V 395
EVI27  329  L P P - - - - I K V L V V Y P S - E I C E H H T I 348
```

Fig. 6A

```
ILI7R  396 L K F A Q F L L T A G G T E V A L D L L E E Q A I 420
EVI27  349 C Y F T E F L Q N H C R S E V I L E K W Q K K R I 373

ILI7R  421 S E A G V M T W V G R Q K Q E M V E S N S K I I V 445
EVI27  374 A E M G P V Q W L A T Q K K - - - - A A D K V V F 394

ILI7R  446 I C S R G T R A K W Q A L L G R G A P V R L R C D 470
EVI27  395 I L S N D V N S V C D G T C G K S E G S - - - - - 414

ILI7R  471 H G K P V G D L F T A A M N M I L P D F K R P A C 495
EVI27  415 P S E N S Q D L F P L A F N L F C S D L R S Q I H 439

ILI7R  496 F G T Y V V C Y F S E V S C D C D V P D L F G A A 520
EVI27  440 L H K Y V V V Y F R E I D T K D D Y N A L S - V C 464

ILI7R  521 P R Y P L M D R F E E V Y F R I Q D L E M F Q P G 545
EVI27  465 P K Y H F M K - - - - - - - - - - D A T A F C A E 478

ILI7R  546 R M H R V G E L S G D N Y L R S P G G R Q L R A A 570
EVI27  479 L L H V K Q Q V S - - - - - - - A G K R S Q - - - 493

ILI7R  571 L D R F R D W Q V R C P D W F E C E N L Y S A D D 595
EVI27  494 - - - - - - - - - A C H D G - - C C S L         502
                                                    (SEQ ID NO: 5)

ILI7R  596 Q D A P S L D E E V F E E P L L P P G T G I V K R 620
ILI7R  621 A P L V R E P G S Q A C L A I D P L V G E E G G A 645
ILI7R  646 A V A K L E P H L Q P R G Q P A P Q P L H T L V L 670
ILI7R  671 A A E E G A L V A A V E P G P L A D G A A V R L A 695
ILI7R  696 L A G E G E A C P L L G S P G A G R N S V L F L P 720
ILI7R  721 V D P E D S P L G S S T P M A S P D L L P E D V R 745
ILI7R  746 E H L E G L M L S L F E Q S L S C Q A Q G G C S R 770
ILI7R  771 P A M V L T D P H T P Y E E E R Q S V Q S D Q G 795
ILI7R  796 Y I S R S S P Q P P E G L T E M E E E E E E E Q D 820
ILI7R  821 P G K P A L P L S P E D L E S L R S L Q R Q L L F 845
ILI7R  846 R Q L Q K N S G W D T M G S E S E G P S A         866
                                                    (SEQ ID NO: 9)
```

Fig. 6B

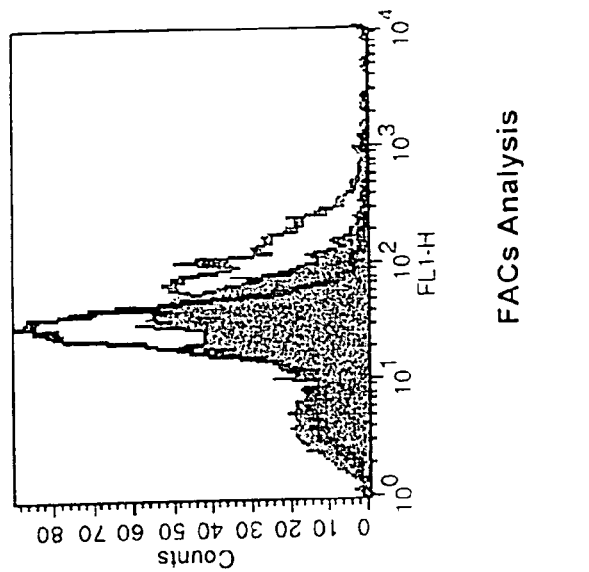
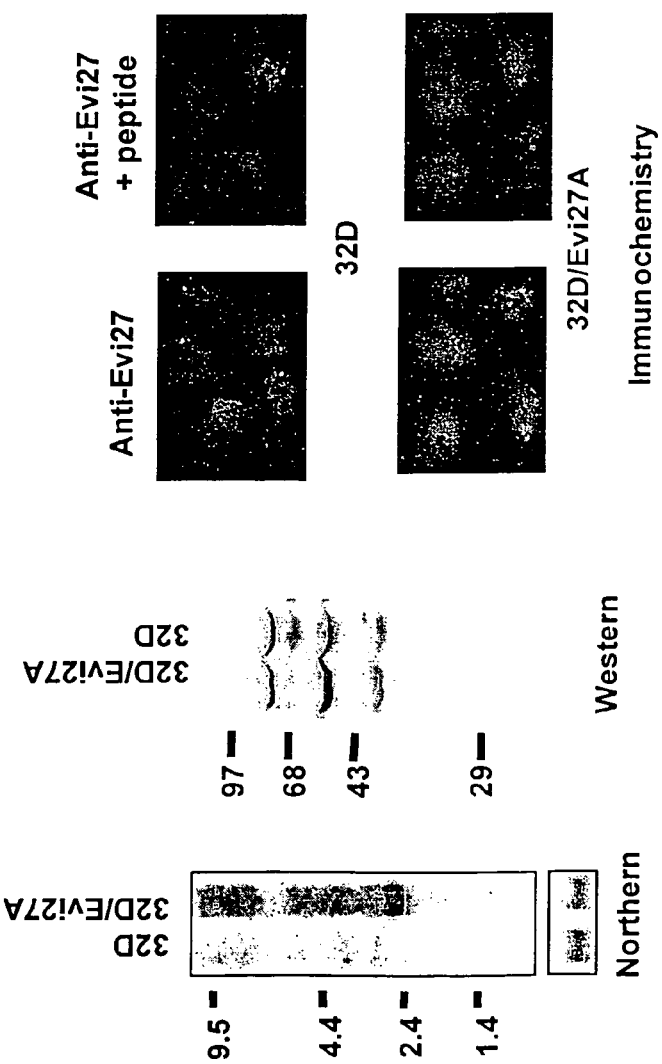
Fig. 8A   Fig. 8B   Fig. 8C   Fig. 8D

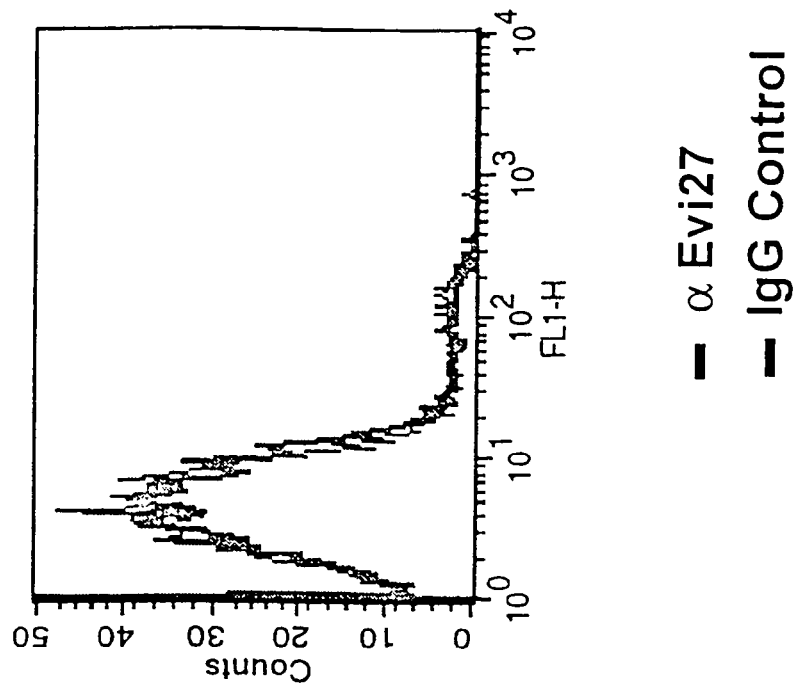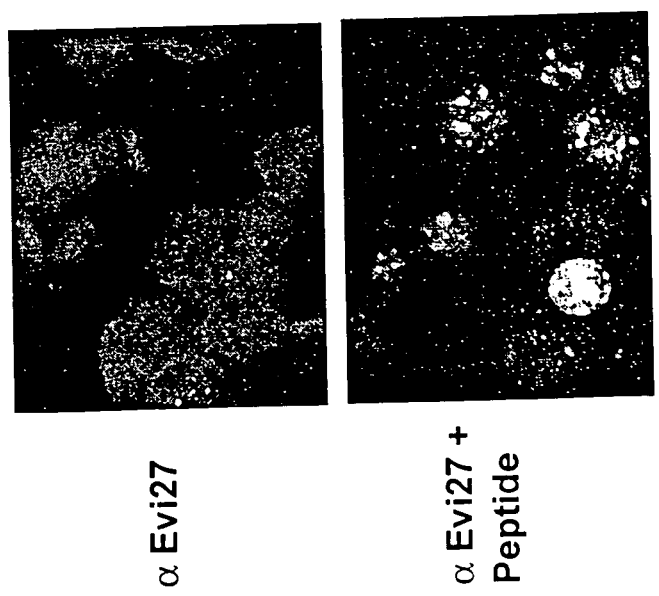
Fig. 11

MODULATION OF THE ACTIVITY OF AN INTERLEUKIN 17 RECEPTOR-RELATED PROTEIN, EVI27, AND USES THEREOF

CROSS-REFERENCE TO RELATED APPLICATION

This patent application is a divisional of U.S. Ser. No. 09/778,971 filed Feb. 2, 2001, which claims benefit of provisional patent application U.S. Ser. No. 60/180,374, filed Feb. 4, 2000.

FEDERAL FUNDING LEGEND

This invention was produced in part using funds obtained through a grant from the National Cancer Institute. Consequently, the federal government has certain rights in this invention.

BACKGROUND OF THE INVENTION

1. Field of the Invention

The present invention relates generally to the field of molecular biology. More specifically, the present invention relates to the cloning and characterization of a murine and human gene that encodes a novel protein with homology to the IL-17 receptor.

2. Description of the Related Art

Retroviral insertional mutagenesis in BXH2 and AKXD recombinant inbred (RI) mice induces a high incidence of myeloid leukemia and the proviral integration sites in the leukemias provide powerful genetic tags for disease gene identification (Bedigian et al., 1984; Gilbert et al., 1993). During the past several years, a number of disease genes have been identified in these leukemias by proviral tagging. These disease genes include a tumor suppressor gene, neurofibromatosis type I (Nf1); a gene with homology to the lymphoid-restricted type II membrane protein Jaw1, Mrv integration site 1 (Mrvi1); a gene encoding a hematopoietic cell growth and differentiation factor, myeloblastosis oncogene (Myb); three homeobox genes, homeobox A7 (Hoxa7), homeobox A9 (Hoxa9), and myeloid ecotropic viral integration site 1 (Meis1); a zinc-finger protein (Evi1); and a gene with homology to the ubiquitin-specific protease 8 (Usp8) oncogene and to genes encoding various cell cycle regulatory proteins, ecotropic viral integration site 5 (Evi5) (Buchberg et al., 1990, Viskochil et al., 1990, Shaughnessy et al., 1999; Copeland and Jenkins, 1999, Nakamura et al., 1996a, Morishita et al., 1988, Liao, et al., 1997). Four of the genes are proven or suspected human disease genes: EVI1, NF1 and HOXA9 are causally associated with myeloid leukemia and EVI5 with stage 4S neuroblastoma (Ogawa et al., 1996, Copeland and Jenkins, 1999, Nakamura et al., 1996b, Roberts et al. 1998), validating the usefulness of this approach for human disease gene identification.

Although proviral tagging has identified many disease genes, it is apparent that several more genes remain to be cloned. This is suggested by the fact only 45% of BXH2 leukemias contain a virally induced mutation in one of the genes identified so far. Disease genes for 55% of BXH2 leukemias remain to be identified. The same is true for human acute myeloid leukemias (AMLs) where the 11 different chromosomal translocations and inversions cloned to date are found in only 45% of acute myeloid leukemias (Look, 1997). Disease genes for 55% of acute myeloid leukemias remain to be identified. Ultimately, it should be possible to use proviral tagging to do a saturation screen for BXH2 disease genes. The expectation is that some of these genes will represent human acute myeloid leukemias genes that are not easy to clone because they are infrequently involved in human disease or are not marked by a cytologically detectable rearrangement. Given the large number of genes that may remain to be identified, this task could be difficult using conventional proviral tagging approaches, which rely on cloning leukemia-specific proviral integration sites into bacteriophage lambda.

With this potential problem in mind, an inverse PCR (IPCR) method for proviral tagging was developed that makes use of automated DNA sequencing and the genetic tools provided by the Mouse Genome Project, which greatly increases the throughput of proviral tagging for disease gene identification. More than 400 proviral integration sites from BXH2 myeloid leukemias (and AKXD T- and B-cell leukemias) were cloned and characterized using this inverse PCR method (Li et al., 1999), which lead to the identification of more than 90 new candidate leukemia disease genes (Li et al., 1999). Nineteen new common integration sites (sites that are targets of viral integration in more than one leukemia) were also identified in these studies and BLAST search and/or chromosome mapping identified candidate disease genes for 12 of these common sites (Li et al., 1999).

One common integration site identified by the inverse PCR is Evi27 (Li et al., 1999). While BLAST searches did not identify a candidate disease gene for Evi27, chromosome mapping studies showed that Evi27 maps to mouse chromosome 14 in a region of human 3p21 homology (Copeland et al., 1993). This result is interesting because treatment-related 3p21 breaks are often observed in myelodysplastic syndrome (MDS) and AML patients (Shi et al., 1996) and 3p21 is the most frequently deleted region seen in chronic myeloid leukemia (CML) (Johansson et al., 1997). Evi27 may be, therefore, an important human disease gene.

The prior art is deficient in lack of the characterization a novel cytokine receptor-related gene whose expression is upregulated by viral integration at Evi27. The present invention fulfills this long-standing need and desire in the art.

SUMMARY OF THE INVENTION

The present invention describes the cloning and sequences of a novel IL-17 receptor-related gene in human and mouse whose expression is upregulated by viral integration in a murine acute myeloid leukemia. Gene transcription and protien expression were examined by northern blot analysis, western blot analysis and immunohistochemical staining. The gene disclosed herein may facilitate myeloid cell transformation and be involved in human disease.

BRIEF DESCRIPTION OF THE DRAWINGS

The appended drawings have been included herein so that the above-recited features, advantages and objects of the invention will become clear and can be understood in detail. These drawings form a part of the specification. It is to be noted, however, that the appended drawings illustrate preferred embodiments of the invention and should not be considered to limit the scope of the invention.

FIG. 4 shows an alignment of mouse and human Evi27 proteins. The putative signal peptide, transmembrane domain, and peptide used to generate polyclonal antisera are indicated by a black line over the sequence. Conserved protein motifs are indicated by a double line. Conserved amino acids are boxed with amino acid identities noted in bold. Normal typeface letters represents conservative amino acid changes. Gaps created in the sequences to optimize alignments are indicated by a dash in the sequence string. Abbreviations: N-GLY, N-linked glycosylation; GSK, kinase phosphorylation site.

FIGS. 6A-6B show an alignment of the human EVI27 and IL-17R proteins. Conserved amino acids are boxed with amino acid identities noted in bold. Gaps created in the sequences to optimize alignments are represented by dashes. Amino acid positions are indicated to the right and left of the sequence.

FIGS. 8A-8D show immunofluorescence and Northern blot analysis of Evi27 expression in murine cell line. The 2.7 kb cDNA coding for the 55 kD isoform of the membrane bound form of the murine Evi27 gene was cloned into a eukaryotic expression plasmid vector and transfected into the murine myeloid leukemia cell line 32D. A cell line was established by limiting dilution and called 32DEvi27A. FIG. 8A shows a Northern blot hybridization of poly-A mRNA from 32D and 32D/Evi27A stable transfectants. Note the abundant expression of the transgene in the transfectant and the absence of expression in the parental line. The blot was also hybridized with a b-actin probe to control for RNA loading. The size in kb of molecular weight markers is show on the left of each panel. FIG. 8B shows Western bolt analysis of same cell lines with affinity purified anti-Evi27 antisera. The transfectant shows overexpression of a 55 kD protein as expected from predicted mRNA translation of the 2.7 kb Evi27 cDNA. Markers in kD are to the left. FIG. 8C shows immunofluorescence staining of the Evi27 protein (red) in the myeloid cell line 32D (top panel) and 32D cells transfected with an Evi27 cDNA expression construct (lower panel). Note the light staining in the parental line and abundant staining in the transfectant (left panels). Nuclei are stained blue with DAPI. Cells were also stained with Evi27 antibody preincubated with Evi27 peptide (right panels). Note that no red staining is evident, demonstrating specificity of the antisera. FIG. 8D shows cell surface expression of Evi27 by flow activated cell sorting analysis (red: anti-Evi27; blue: anti-Evi27+peptide; green: IgG control).

FIG. 11 shows abundant Evi27 protein was found in the cytoplasm, but not on the cell surface, in the myeloid leukemia B160. The left panel shows immunochemistry of the B160 cells with the anti-Evi27 antibody before and after pre-treatment with Evi27 peptide. Evi27 is expressed in the cytoplasm at high concentration. Right panel shows FACs analysis with anti-Evi27, indicating Evi27 is not expressed on the cell surface (red: anti-Evi27; black: IgG control).

DETAILED DESCRIPTION OF THE INVENTION

Figure 1:
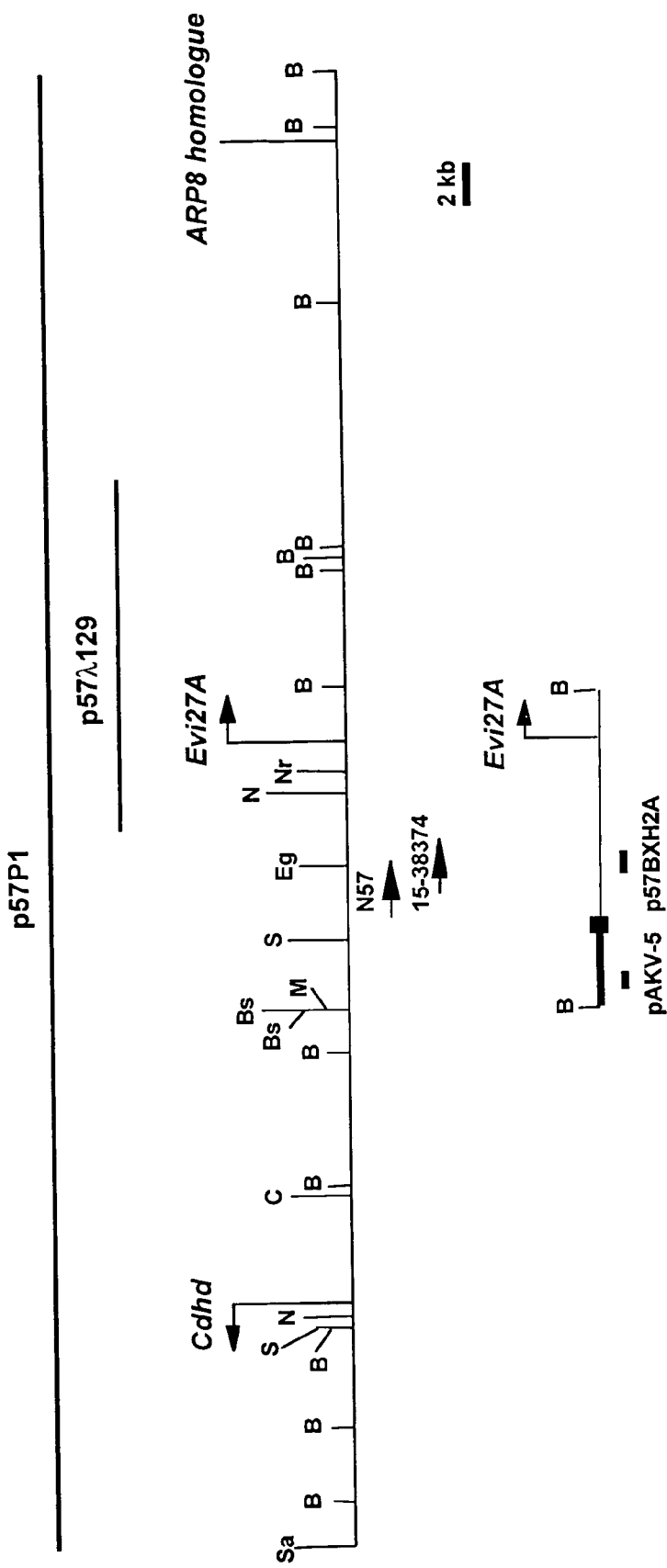
FIG. 1 shows a partial long-range restriction map of the Evi27 locus. Bacteriophage 1 and P1 clones used for gene localization and exon trapping are shown above the map. The location of the 5' end and transcriptional orientation of the Evi27 and Cdhd genes are noted by arrows above the map. The location of the exon with homology to the yeast ARP8 gene is also noted. The transcriptional orientation of this gene has not been determined. The position and transcriptional orientation of the proviruses in the B160 and 15-38374 leukemias are indicated below the map. The cluster of rare cutting restriction enzymes surrounding the proviral integration sites is also noted. The 14 kb BamHI fragment cloned from leukemia B160 is presented below the map. The viral sequences and viral long terminal repeat (LTR) is noted by a thick line and black box, respectively. The position of the 5' end of Evi27 with respect the viral LTR is noted. Restriction enzymes: B, BamHI; Bs, BssHII; C, ClaI; E, EagI; M, MluI, N, NaeI; Nr, NruI, S, SacII; Sa, SalI.

Evi27 is a common site of retroviral integration in BXH2 murine myeloid leukemias. The present invention shows that integration at Evi27 occurs in a CpG island ~6 kb upstream from a novel gene (designated Evi27) with homology to the IL17 receptor (Il17r) and that proviral integrations result in increased Evi27 expression. The human EVI27 homologue was also cloned and mapped to chromosome 3p21. Multiple Evi27 isoforms were detected at the RNA and protein level in both human and mouse, indicating that Evi27 expression is complex. Some of the isoforms are shown to likely represent secreted soluble forms of the protein produced by intron incorporation or by proteolytic cleavage. In the mouse, highest Evi27 expression occurs in liver and testes with lower expression in kidney and lung. In humans, EVI27 is expressed at high levels in the kidney, with moderate levels in the liver, brain, and pancreas. Within hematopoietic cells, Evi27 expression is restricted. Northern and Western analysis showed that Evi27 is expressed in selected T-cell, B-cell and myeloid cell lines. These results suggest that Evi27 expression is tightly regulated during hematopoietic differentiation. Collectively, these studies identify a new member of the cytokine receptor family whose increased and uncoordinated expression may lead to myeloid leukemia by altering Evi27's normal ability to control the growth and/or differentiation of hematopoietic cells.

In accordance with the present invention, there may be employed conventional molecular biology, microbiology, and recombinant DNA techniques within the skill of the art. Such techniques are explained fully in the literature. See, e.g., Sambrook, Fritsch & Maniatis, "Molecular Cloning: A Laboratory Manual (2nd Ed.)", (1989); "DNA Cloning: A Practical Approach," Volumes I and II (D. N. Glover ed. 1985); "Oligonucleotide Synthesis" (M. J. Gait ed. 1984); "Nucleic Acid Hybridization" [B. D. Hames & S. J. Higgins eds. (1985)]; "Transcription and Translation" [B. D. Hames & S. J. Higgins eds. (1984)]; "Animal Cell Culture" [R. I. Freshney, ed. (1986)]; "Immobilized Cells And Enzymes" [IRL Press, (1986)]; B. Perbal, "A Practical Guide To Molecular Cloning" (1984). Therefore, if appearing herein, the following terms shall have the definitions set out below.

A "DNA molecule" refers to the polymeric form of deoxyribonucleotides (adenine, guanine, thymine, or cytosine) in its either single stranded form or a double-stranded helix. This term refers only to the primary and secondary structure of the molecule, and does not limit it to any particular tertiary forms. Thus, this term includes double-stranded DNA found, inter alia, in linear DNA molecules (e.g., restriction fragments), viruses, plasmids, and chromosomes. DNA structures are discussed herein according to the normal convention of giving only the sequence in the 5' to 3' direction along the nontranscribed strand of DNA (i.e., the strand having a sequence homologous to the mRNA). The term "peptide" or "polypeptide" is defined as several (i.e., multiple) amino acids attached together.

A "vector" is a replicon, such as plasmid, phage or cosmid, to which another DNA segment may be attached so as to bring about the replication of the attached segment. A "replicon" is any genetic element (e.g., plasmid, chromosome, virus) that functions as an autonomous unit of DNA replication in vivo; i.e., capable of replication under its own control. An "origin of replication" refers to those DNA sequences that participate in or direct DNA synthesis. An "expression control sequence" is a DNA sequence that controls and regulates the transcription and translation of another DNA sequence. A coding sequence is "operably linked" and "under the control" of transcriptional and translational control sequences in a cell when RNA polymerase transcribes the coding sequence into mRNA, which is then translated into the protein encoded by the coding sequence.

In general, expression vectors containing promoter sequences which facilitate the efficient transcription and translation of the inserted DNA fragment are used in connection with a particular host. The expression vector typically contains an origin of replication, promoter(s), terminator(s), as well as specific genes which are capable of providing phenotypic selection in transformed cells (i.e., selectable markers). The transformed hosts can be fermented and cultured according to means known in the art to achieve optimal cell growth.

A DNA "coding sequence" is a double-stranded DNA sequence which is transcribed and translated into a polypeptide in vivo when placed under the control of appropriate regulatory sequences. Specifically as used herein, "DNA coding for a protein" means DNA sequences which produce a particular primary amino acid sequence. The boundaries of the coding sequence are determined by a start codon at the 5' (amino) terminus and a translation stop codon at the 3' (carboxyl) terminus. A coding sequence can include, but is not limited to, prokaryotic sequences, a cDNA from eukaryotic mRNA, genomic DNA sequences from eukaryotic (e.g., mammalian) organisms and even synthetic DNA sequences. A polyadenylation signal and transcription termination sequence will usually be located 3' of the coding sequence. A "cDNA" is defined as copy DNA or complementary DNA and is a product of a reverse transcription reaction from an mRNA transcript. An "exon" is an expressed sequence transcribed from the gene locus, whereas an "intron" is a non-expressed sequence that is from the gene locus.

Transcriptional and translational control sequences are DNA regulatory sequences, such as promoters, enhancers, polyadenylation signals, terminators, and the like, that provide for the expression of a coding sequence in a host cell. A "cis-element" is a nucleotide sequence, also termed a "consensus sequence" or "motif", that interacts with proteins that upregulate or downregulate expression of a specific gene locus. A "signal sequence" can also be included with the coding sequence. This sequence encodes a signal peptide, N-terminal to the polypeptide, that communicates to the host cell and directs the polypeptide to the appropriate cellular location. Signal sequences can be found associated with a variety of proteins native to prokaryotes and eukaryotes.

A "promoter sequence" is a DNA regulatory region capable of binding RNA polymerase in a cell and initiating transcription of a downstream (3' direction) coding sequence. Specifically as used herein, the term "promoter(s)" means regulatory DNA sequences that control transcription of the cDNA. For purposes of defining the present invention, a minimal promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site, as well as protein binding domains (consensus sequences) responsible for the binding of RNA polymerase. Eukaryotic promoters often, but not always, contain "TATA" boxes and "CAT" boxes. Prokaryotic promoters contain the −10 and −35 consensus sequences, and additionally, ribosomal binding Shine-Dalgarno sequences. As used herein, "promoter" may also refer to an intact regulatory sequence directing transcription (and subsequent translation) of a coding sequence, and may include any or all of the above-mentioned transcriptional and translational control sequences.

The term "oligonucleotide" is defined as a molecule comprised of two or more deoxyribonucleotides, preferably more than three. Its exact size will depend upon many factors which, in turn, depend upon the ultimate function and use of the oligonucleotide. The term "primer" as used herein refers to an oligonucleotide, whether occurring naturally as in a purified restriction digest or produced synthetically, which is capable of acting as a point of initiation of synthesis when placed under conditions in which synthesis of a primer extension product, which is complementary to a nucleic acid strand, is induced, i.e., in the presence of nucleotides and a polymerizing agent, such as a DNA polymerase, and at a suitable temperature and pH. The primer may be either single-stranded or double-stranded and must be sufficiently long to prime the synthesis of the desired extension product in the presence of the polymerizing agent. The exact length of the primer will depend upon many factors, including temperature, source of primer and use the method. For example, for diagnostic applications, depending on the complexity of the target sequence, the oligonucleotide primer typically contains 15-25 or more nucleotides, although it may contain fewer nucleotides.

"Recombinant DNA technology" refers to techniques for uniting two heterologous DNA molecules, usually as a result of in vitro ligation of DNAs from different organisms. Recombinant DNA molecules are commonly produced by experiments in genetic engineering. Synonymous terms include "gene splicing", "molecular cloning" and "genetic engineering". The product of these manipulations results in a "recombinant" or "recombinant molecule".

A cell has been "transformed" or "transfected" with exogenous or heterologous DNA when such DNA has been introduced into the cell. Specifically as used herein, the term "transformation" or "transfection" means incorporation permitting expression of heterologous DNA sequences by a cell. The transforming DNA may or may not be integrated (covalently linked) into the genome of the cell. In prokaryotes, yeast, and mammalian cells, the transforming DNA may be maintained on an episomal element such as a vector or plasmid. With respect to eukaryotic cells, a stably transformed cell is one in which the transforming DNA has become integrated into a chromosome so that it is inherited by daughter cells through chromosome replication. This stability is demonstrated by the ability of the eukaryotic cell to establish cell lines or clones comprised of a population of daughter cells containing the transforming DNA. A "clone" is a population of cells derived from a single cell or ancestor by mitosis. A "cell line" is a clone of a primary cell that is capable of stable growth in vitro for many generations. An organism, such as a plant or animal, that has been transformed with exogenous DNA is termed "transgenic".

As used herein, the term "host" is meant to include not only prokaryotes, but also eukaryotes such as yeast, plant and animal cells. Specifically as used herein, the term "host(s)" means any cell that will allow or direct expression. Specifically as used herein, "chimeric cell" means a cell whose DNA has been altered compared to a normal cell of the same organism. A recombinant DNA molecule or gene can be used to transform a host using any of the techniques commonly known to those of ordinary skill in the art. Prokaryotic hosts may include *E. coli, S. tymphimurium, Serratia marcescens* and *Bacillus subtilis*. Eukaryotic hosts include yeasts such as *Pichia pastoris*, mammalian cells and insect cells, and plant cells, such as *Arabidopsis thaliana* and *Tobaccum nicotiana*.

As used herein, "fragment," as applied to a polypeptide, will ordinarily be at least 10 amino acid residues, more typically at least 20 residues, and preferably at least 30 (e.g., 50) residues in length, but less than the entire, intact sequence. Fragments can be generated by methods known to those skilled in the art, e.g., by enzymatic digestion of naturally occurring or recombinant protein, by recombinant DNA techniques using an expression vector that encodes a defined fragment, or by chemical synthesis. Purified fragments or antigenic fragments can be used to generate antibodies employing standard protocols known to those skilled in the art. As used herein, "functional fragment" is meant to encompass those peptide fragments retaining biological activity of Evi27.

Due to the redundancy of the DNA code, there are millions of DNA sequences that would produce the same amino acid sequence when expressed. Given an amino acid sequence, one can substitute into the natural DNA sequence alternative codons for the desired amino acids to produce an alternative DNA sequence also coding for the novel protein. One may find that particular chimeric cells of a particular expression method favor particular mRNA codons for a particular amino acid. Altering the human DNA sequence to increase the frequency of favored codons may improve the expression efficacy in a chimeric cell, thus improving the efficacy of the expression process. The sequences may be derived by substitution of redundant codons for the amino acid sequences and splicing the substituted sequences into the natural gene by routine methods well known in the art. Those skilled in the art will recognize that many variations are possible in substituting conserved amino acids in the protein sequence which will produce variations in sequence without seriously changing the biological activity of the protein. It is impractical to attempt to list all the millions of DNA sequences that may code for the claimed sequence. However, the invention comprises the novel protein, its novel amino acid sequence, and all DNA sequences natural or synthetic coding for the novel amino acid sequence.

These substitution analogs may be constructed in the following manner: Table 1 lists the alternative codons that code for the 20 common amino acids. DNA sequence substitution analogs that also code for human can be constructed by choosing alternate codons from Table 1 to alter the DNA sequence between a pair of restriction enzyme cleavage sites, as are well known in the art. Alternative codons are assembled into a synthetic oligonucleotide by conventional methods and the synthetic oligo is substituted into the endonuclease treated DNA by the methods described in "Molecular Cloning. A Laboratory Manual", 2d Edition, Cold Spring Harbor Laboratory Press (1989), to produce a substitution analog. Other methods generally known to those skilled in the art can also be employed to obtain substitution analogs of DNA sequences.

The alteration of the DNA by cleavage and codon substitution may be repeated to substitute substantial portions of the original DNA sequence with alternative codons without altering the protein amino acid sequence. Alteration of a DNA sequence which produces no change in the protein expressed by the DNA sequence might, for example, be conducted to increase protein expression in a particular host cell by increasing the occurrence of codons that correspond to amino acid tRNAs found in higher concentration in the host cell. Such altered DNA sequences for substitution analogs can be easily produced by those of ordinary skill in the art following the method set out above, or other alternative techniques for altering the DNA sequence while obtaining the same protein on expression. Substitution analogs can be obtained by substitution of oligonucleotides at restriction cleavage sites as described above, or by other equivalent methods that change the codons while preserving the amino acid sequence of the expressed protein.

of a gene in accordance with conventional Southern hybridization techniques known to those of ordinary skill in the art. Both the Northern blot and Southern blot use a hybridization probe, (e.g., radiolabelled full-length or partial cDNA) of at least 20 (preferably at least 30, more preferably at least 50, and most preferably at least 100) consecutive nucleotides in length. The DNA hybridization probe can be labelled by any of the many different methods known to those skilled in this art.

The labels most commonly employed for these studies are radioactive elements, enzymes, chemicals which fluoresce when exposed to untraviolet light, and others. A number of fluorescent materials are known and can be utilized as labels. These include, for example, fluorescein, rhodamine, auramine, Texas Red, AMCA Blue and Lucifer Yellow. Proteins can also be labeled with a radioactive element or with an enzyme. The radioactive label can be detected by any of the currently available counting procedures. The preferred isotope may be selected from $^{3}H$, $^{14}C$, $^{32}P$, $^{35}S$, $^{36}Cl$, $^{51}Cr$, $^{57}Co$, $^{58}Co$, $^{59}Fe$, $^{90}Y$, $^{125}I$, $^{131}I$, and $^{186}Re$.

TABLE 1

| SYMBOL | | | |
|---|---|---|---|
| 1-Letter | 3-Letter | AMINO ACID | CODON USAGE |
| A | Ala | Alanine | GCT, GCC, GCA, GCG |
| C | Cys | Cysteine | TGT, TGC |
| D | Asp | Aspartic acid | GAT, GAC |
| E | Glu | Glutamic acid | GAA, GAG |
| F | Phe | Phenylalanine | TTT, TTC |
| G | Gly | Glycine | GGT, GGC, GGA, GGG |
| H | His | Histidine | CAT, CAC |
| I | Ile | Isoleucine | ATT, ATC, ATA |
| K | Lys | Lysine | AAA, AAG |
| L | Leu | Leucine | TTA, TTG, CTT, CTC, CTA, CTG |
| M | Met | Methionine | ATG |
| N | Asn | Asparagine | AAT, AAC |
| P | Pro | Proline | CCT, CCC, CCA, CCG |
| Q | Gln | Glutamine | CAA, CAG |
| R | Arg | Arginine | CGT, CGC, CGA, CGG, AGA, AGG |
| S | Ser | Serine | TCT, TCC, TCA, TCG, AGT, AGC |
| T | Thr | Threonine | ACT, ACC, ACA, ACG |
| V | Val | Valine | GTT, GTC, GTG, GTG |
| W | Trp | Tryptophan | TTG |
| Y | Tyr | Tyrosine | TAT, TAC |

As described herein, a standard Northern blot assay can be used to ascertain the relative amounts of mRNA in a cell or tissue in accordance with conventional Northern hybridization techniques known to those persons of ordinary skill in the art. Alternatively, a standard Southern blot assay may be used to confirm the presence, the copy number and/or the position Enzyme labels are likewise useful, and can be detected by any of the presently utilized colorimetric, spectrophotometric, fluorospectrophotometric, amperometric or gasometric techniques. The enzyme is conjugated to the selected particle by reaction with bridging molecules such as carbodiimides, diisocyanates, glutaraldehyde and the like. Many enzymes which can be used in these procedures are known and can be utilized. The preferred are peroxidase, β-glucuronidase, β-D-glucosidase, β-D-galactosidase, urease, glucose oxidase plus peroxidase and alkaline phosphatase. U.S. Pat. Nos. 3,654,090, 3,850,752, and 4,016,043 are referred to by way of example for their disclosure of alternate labeling material and methods.

The present invention is directed to an isolated nucleic acid molecule encoding an IL-17 receptor-related protein selected from the group consisting of: (a) an isolated nucleic acid molecule of SEQ. ID NO: 1, 2, 3 or 4 which encodes an IL-17 receptor-related protein; (b) an isolated nucleic acid molecule which is complimentary and hybridizes to the nucleic acid molecules of (a); and (c) isolated nucleic acid molecule differing from the isolated nucleic acid molecules of (a) or (b) in codon sequence due to the degeneracy of the genetic code, and which encodes an IL-17 receptor-related protein.

In one embodiment, there is provided a fragment of one of the nucleic acid molecules listed above that is at least 10 bases long and which will selectively hybridize to nucleic acid molecule encoding an IL-17 receptor-related protein. Preferably, the nucleic acid molecule may be used as an anti-sense molecule to inhibit the expression of an IL-17 receptor-related protein, for chromosomal mapping or mutation analysis of gene encoding an IL-17 receptor-related protein.

The present invention is also directed to a genomic DNA encoding an IL-17 receptor-related protein, wherein said genomic DNA hybridizes to the nucleic acid molecules described above.

The present invention is also directed to vector comprising a nucleic acid molecule of SEQ. ID NO: 1, 2, 3 or 4 and cells transfected with the vector. Representative cells include bacterial cells, mammalian cells, plant cells and insect cells.

The present invention is also directed to an IL-17 receptor-related protein, or a peptide derived thereof, encoded by nucleic acid molecule of SEQ ID No. 3 or 4, wherein said protein is about 24, 33, 56, 47, 75, 127, and 150 kD in size as detected by western blot analysis in BXH2 leukemia cell. The present invention is further directed to an IL-17 receptor-related protein, or a peptide derived thereof, encoded by the nucleic acid molecules disclosed herein, wherein said protein has the amino acid sequence of SEQ. ID NO: 5, 6, 7 or 8. Preferably, the peptide is at least 4 amino acids long. The peptides can be used to generate anti-Evi27 antibody, and a person having ordinary skill in the art would be readily able to prepare an antibody that binds specifically to any of these proteins or peptides.

The present invention is also directed to a method of stimulating the secretion of cytokines from a cell, comprising the step of binding a ligand to the IL-17 receptor-related protein, Evi27. In general, Evi27 stimulation can lead to the secretion of IL-1, IL-8 and TNF-a from hematopoietic cells, leukemia cells and kidney cells.

The present invention is also directed to a method of modulating the expression and activity of an IL-17 receptor-related protein, Evi27, comprising the step of contacting a molecule to a cell, wherein the binding of said molecule to Evi27 mRNA or protein results in increased or decreased expression and activity of the Evi27 protein. Preferably, the molecule can be anti-sense oligonucleotides, small molecule that binds to Evi27, modified IL-17E or soluble form of the Evi27 receptor.

The following examples are given for the purpose of illustrating various embodiments of the invention and are not meant to limit the present invention in any fashion:

EXAMPLE 1

BXH2 Mice and Leukemic Cell Lines

The BXH2 recombinant inbred strain was obtained from the Jackson Laboratory (Bar Harbor, Me.) and maintained at the NCI-Frederick Cancer Research and Development Center. BXH2 leukemia cell lines have been previously described (Largaespada et al., 1995). Other cell lines were purchased from the ATCC and grown in either RPMI 1640 or DMEM supplemented with 2 mM glutamine, 4.5 g/L glucose, Pen-Strep, and 10% fetal bovine serum (Atlanta Biologicals, Atlanta Ga.).

EXAMPLE 2

DNA Extraction and Southern Blot Hybridization

High molecular weight genomic DNAs were extracted from frozen normal tissues and leukemic spleens and lymph nodes as previously described (Jenkins et al., 1982). Bacteriophage and plasmid DNAs were purified using standard procedures (Sambrook et al., 1987). Restriction enzyme digestions, agarose gel electrophoresis, Southern blot transfers, hybridizations, and washes were performed as previously described (Sambrook et al., 1987).

EXAMPLE 3

Genomic Cloning 70 mg of DNA from leukemia N57 was digested to completion with BamHI and fractionated by electrophoresis in TAE buffer. Fragments approximating the somatically acquired pAKV5 (ecotropic murine leukemia virus) hybridizing fragments were cut from the gel and purified using Qiaex beads according to the manufacturer's instructions (Qiagen, Valencia, Calif.). The BamHI fragments were cloned into EMBL4 phage arms (Stratagene, La Jolla, Calif.). Ligated material was packaged with Gigapack Gold packaging extracts (Stratagene, La Jolla, Calif.). Library screening was performed according to the protocol of Benton and Davis (1977). The P1 and lambda genomic clones were derived from commercial libraries (Genome Systems, St. Louis, Mo., Clontech, Palo Alto, Calif.).

EXAMPLE 4

Human Chromosome Mapping

Metaphase chromosomes from normal peripheral blood samples were prepared using conventional methods. Slides were incubated in 2×SSC (pH 7.0, 37° C.) for 15 minutes then immersed in 0.1N HCl/0.05% Triton X-100 for 15 minutes at room temperature (RT). Slides were washed in 2×SSC (pH 7.0) twice at room temperature, then washed in 1×PBS, pH 7.2 once at room temperature. Slides were immersed in 1% formaldehyde (diluted in PBS) for 10 minutes at room temperature, washed twice in 1×PBS at room temperature, then once in 2×SSC (pH 7.0) at room temperature. Chromosomes were dehydrated in an ethanol series and air dried at room temperature.

A human PAC clone specific for EVI27 was isolated by screening a human P1 artificial chromosome (PAC) library according to the manufacturer's instructions and high molecular weight PAC DNA was isolated using the KB-100 kit (Genome Systems, St. Louis, Mo.). Spectrum-Red-dUTP (Vysis, Downer's Grove, Ill.) was incorporated into PAC/BAC probes by nick translation according to the manufacturer's protocol (Vysis, Downer's Grove, Ill.). DNA was resuspended in Hybrisol VII (Oncor, Gaithersburg, Md.) (50% formamide/2×SSC) at a final concentration of 5 ng/ul and hybridized to chromosomes according to manufacturer's instructions. The chromosomes and probe solution was incubated at 75° C. for 10 minutes. then to 37° C. for 16 hrs in a humidified chamber. Post hybridization washes consisted of 65% formamide/2×SSC (pH 7.0) for 15 minutes at 43° C., then 2×SSC (pH 7.0) for 8 minutes at 37° C., 1×PBD (Oncor, Gaithersburg Md.) twice at room temperature, then in 1×PBS (pH 7.2). Finally, 10 ml of propidium iodide/antifade (1:20) was added on each area and a coverslip added. Following FISH, the slide was washed twice in Xylene to remove the coverslip and excess oil. The slide was then washed in 1×PBD at 37° C. for 5 minutes followed by a dehydration step through an ethanol series. The slide was then incubated in 50% formamide/2×SSC for 90 minutes at 37° C., washed briefly in tap water, followed by dehydration in 10, 80, and 95% ethanol and stained with Wright's stain/phosphate buffer for 5 minutes.

EXAMPLE 5

Exon Trapping

The P1 clone p57P1 was digested to completion with BglII and BamHI and purified by phenol extractions and ethanol precipitations. Insert DNA was then ligated to a BamHI digested pSPL3 vector (Life Technologies, Gaithersburg, Md.). DNA from the ligations was used to transform DH10B maximum efficiency cells (Life Technologies, Gaithersburg, Md.). Additional steps in the experiment were performed exactly according to the manufacuters protocol (Life Technologies). DNA sequence of approximately 100 individual clones from each ligation was generated as described below.

EXAMPLE 6

Poly(A)+ RNA Isolation and Northern Blot Analysis

Premade Northern blots containing 2 mg of twice selected poly(A)+ RNA from various normal tissues and cell lines were purchased from commercial source (CLONTECH, Palo Alto, Calif.). Total RNA was extracted from cell line suspensions by the RNAzol B method (Tel-Test, Friendswood, Tex.). poly(A)+ RNA was purified from the total RNA preps by oligo-d(T) column chromatography according the manufacturers recommendations (Amersham Pharmacia Biotech, Piscataway, N.J.). 2-5 mg of poly(A)+ RNA was fractionated by electrophoresis in 1.0% agarose gels containing formaldehyde and transferred to Hybond N+ membranes (Amersham Pharmacia Biotech, Piscataway, N.J.). The membranes were prehybridized and hybridized according to the method of Church and Gilbert or using ExpressHyb solution (Clontech, Palo Alto, Calif.). Blots were then exposed to X-ray film at −70° C. with an intensifying screen.

EXAMPLE 7 cDNA Cloning cDNA cloning was carried out by a combination of 5' and 3' rapid amplification of cDNA ends (5' and 3' RACE) and modified RT-PCR as described (Shaughnessy et al., 1999). Briefly, the nucleotide sequence of the trapped exon p57P1ET47was used to design specific nested oligonucleotides. The primary 5' and 3' RACE reactions were performed using mouse liver Marathon Ready cDNA (Clontech, Palo Alto, Calif.) as a template according to the manufactures protocol using the Advantage cDNA amplification kit (Clontech, Palo Alto, Calif.). After cloning and sequencing, nested primers specific for the 5' and 3' ends of the gene were synthesized. Another cycle of PCR was performed using Marathon Ready liver cDNA as a template and the full length cDNA was generated by PCR as follows: 1 cycle: 94° C. 1 min; 30 cycles: 94° C., 30 sec, 68° C., 7 min. The products of the reaction were subcloned into pCR2.1 (Invitrogen, Carlsbad, Calif.) and sequenced. The full-length cDNA of the 1.9 kb and 2.7 kb transcripts have been submitted to GenBank under accession numbers AF208108 and AF208109, respectively.

Human cDNAs covering the coding region of the EVI27 gene were synthesized in a similar manner as described above. Briefly, a human EST (accession number T96740), with high homology to the mouse EVI27 cDNA, was used to design nested oligonucleotide primers at the 5' and 3' end of the EST. 5' and 3' RACE products from Marathon Ready fetal liver cDNA (Clontech, Palo Alto, Calif.) were synthesized as described above. The 1.9 kb and 2.9 kb human EVI27 cDNA nucleotide sequences are deposited in GenBank under accession numbers AF208110 and AF208111.

EXAMPLE 8

Transfection and Stable Cell Lines

The 1.9 kb mouse Evi27 cDNA was cloned into the NotI-HindIII site of the pcDNA3.1(−) eukaryotic expression vector and transformed into DH5a bacteria. 10 mg of recombinant plasmid DNA was resuspended at 1 mg/ml in sterile TE. Cell lines 32Dcl3, M1, WEHI3B, and NIH3T3 were grown in appropriate media maintaining cell viability at 90%. Cells were harvested and washed 3× in FBS-free DMEM media. Cells were resuspended at $5 \times 10^6$ cells per ml in FBS-free DMEM. One ml of the cell suspension was mixed with DEAE dextran at 0.1 mg/ml and 10 mg of plasmid DNA in an 0.4 cm electrode gap electroporation cuvette and chilled on ice for 10 minutes and Eletroporated at 270 V/975 mF in a Gene Pulser II (Bio-Rad, Hurcules, Calif.). The cuvette was chilled on ice for 10 minutes then the cells were transferred into 10 ml of fresh media and grown for 72 hrs. G418 selection was carried out in 2 mg/ml for 2 weeks. Limiting dilution cloning in 96 well culture dishes was performed at 1 mg/ml G418 on all cell lines with the exception of NIH3T3. Stable transfectants were cloned and tested for expression of the transgene by Northern blot hybridization.

EXAMPLE 9

Southern and Northern Blot Probes

The b-actin probe was a 2.0 kb cDNA (Clontech, Palo Alto, Calif.). Probes pAKV5 and pEco have been described (Nakamura et al., 1996). p57BXH2A was a 700 bp PCR fragment generated from the flanking DNA from clone p57BXH2. Probe p57ET47was a 103 bp exon trapped from p57 P1. The human intron probe was synthesized by PCR from genomic DNA. Human ESTs were derived from IMAGE consortium clones. Full length 1.9 kb human and mouse Evi27 cDNAs were used in all probes were labeled with [a$^{32}$P]-dCTP using the Prime It II labeling kit (Stratagene, La Jolla, Calif.).

EXAMPLE 10

DNA Sequencing

DNA sequencing was performed using the PRISM Ready Reaction DyeDeoxy Terminator Cycle Sequencing Kit (Perkin Elmer) on the ABI Model 373A DNA Sequencer (Applied Biosystems). Sequence primers were either the T3, T7 sequencing primers or synthetic oligomers derived from previously determined sequence.

EXAMPLE 11

Immunohistochemistry

Cells were harvested and washed once in PBS and resuspended at 1-2×10$^6$ cells per ml in PBS. 0.5 ml of the cell suspension was subjected to cytocentrifugation at 1200×g for 5-10 minutes and air dried for 15-20 minutes, rinsed in PBS and drained well but not allowed to dry. Slides were fixed in fresh 4% paraformaldehyde for 10 minutes followed by two washes in PBS. Cells were permeabilized by incubation in acetone for 30 seconds at RT. Slides were rinsed in PBS with four changes over 5 minutes. Cells were blocked with 5% goat serum in PBS for 30 minutes at RT. The polyclonal anti-peptide EVI27 antibody, 2954, was affinity purified using the Sulfa-Link kit according to manufacturer's instructions (Pierce, Rockford, Ill.). Antibodies were diluted in 1 M HEPES buffer containing 0.15 N NaCl. Sixty microliters of the primary antibody solution was added to slides and incubated for 30 minutes in a humidified chamber at RT. The primary antibody was blocked with 100 mg of peptide by incubating for 1 hour at RT. This solution was then added to the slides as above. After hybridization the slides were washed three times for 5 minutes in 1×PBD (Oncor, Gaithersburg, Md.). The secondary antibody, a rhodamine conjugated goat-anti-rabbit antibody (Pierce, Rockford, Ill.) was diluted in the same buffer as the primary antibody and the solution was added to slides for 30 minutes. Slides were washed 3× in PBS for 5 minutes each wash. The nuclei were counterstained with DAPI at 1/40 dilution in antifade (Oncor, Gaithersburg, Md.), coverslips added and viewed with an Olympus BX60 epifluoresence microscope.

EXAMPLE 12

Western Blotting

Cells were harvested at logarithmic growth stage and washed 2× in 1×PBS. Cells were resuspended in extraction buffer (1×PBS (pH 7.2), 10 mg/ml Aprotinin (0.1 unit/ml), 10 mg/ml Leupeptin, 1 mM PMSF) at 10$^6$cells/100 ml. Protein was extracted by the freeze-thaw method. The solid phase was removed by centrifugation at 12,000 g×10 minutes at 4° C. The aqueous phase was collected concentrated and quantified using the BCA assay kit (Pierce, Rockford, Ill.). Protein separating gels were precast (Novex, San Diego, Calif.). Protein (50-100 mg) was mixed 1:1 with sample buffer (2×) (Novex, San Diego, Calif.), denatured for 15 minutes, cooled to RT and loaded. Gels were run for 2-3 hours at 200V with cooling (60 W initially) in 1× running buffer (25 mM Tris, 192 mM glycine, 0.1% SDS at pH 8.3). Protein was transferred to Hyboond-C super membrane (Amersham Pharmacia Biotech, Piscataway, N.J.) using an electrophoretic blotting system (C.B.S. Scientific Co. Del Mar, Calif.) in 1× transfer buffer (48 mM Tris, 39 mM glycine, 20% methanol) at 100V for 5-6 hrs. The western blot was processed as described (WesternBreeze kit, Novex, San Diego, Calif.).

EXAMPLE 13

Computer DNA and Protein Sequence Analysis

Sequence homology searches were conducted at the protein level using the National Center for Biotechnology Information and the BLAST network service. The DNA and protein sequence alignments and protein motif sequence searches were performed using MacVector (Oxford Molecular Group, Beaverton, Oreg.) and pSORT (Nakai and Kanehisa, 1992).

EXAMPLE 14

Cloning and Characterization of Genomic Sequences from the Evi27 Locus

Genomic restriction analysis of DNA from two BXH2 leukemias with proviral integrations at Evi27 (N57 [B160] and 15-38374) showed that the integrations in the two leukemias are located about 1.5 kb apart and are oriented in the same transcriptional direction (FIG. 1). Lambda and P1 clones from the region were then isolated, restriction mapped and exon trapped. Four exon-trapped products were identified. BLAST searches showed that two of the exons were derived from the mouse choline dehydrogenase (Chdh) gene, while one exon was derived from a gene with high homology to the yeast actin-like protein, ARP8 (accession number S67026). The Chdh gene was subsequently positioned ~10 kb to the left of the proviral integration sites and in the opposite transcriptional direction (FIG. 1). Northern analysis showed that Chdh expression is restricted to liver and is not activated in the B160 cell line (a cell line derived from the N57 leukemia that carries a proviral integration at Evi27). The ARP8 homologue was mapped ~15-20 kb to the right of the proviral integration sites. Northern analysis showed that this gene is ubiquitously expressed and is not upregulated in B 160 leukemia cells. On this basis, Chdh and ARP8 were excluded as candidate disease genes.

The fourth exon (p57ET47) showed no significant homology to any sequences in GeneBank. Hybridization studies showed that this exon was contained within lambda clone p571129 (FIG. 1), indicating that it was located within 5-20 kb of the proviral integration sites at Evi27. DNA sequence analysis of p571129 identified a 103 bp fragment that was homologous to a human fetal liver cDNA EST (accession number T96740). This EST sequence was localized 1240 bp upstream of p57ET47 and was found to be oriented in the same transcriptional direction, suggesting that both exons might be derived from the same gene.

Figures 2A, 2B, 2C:
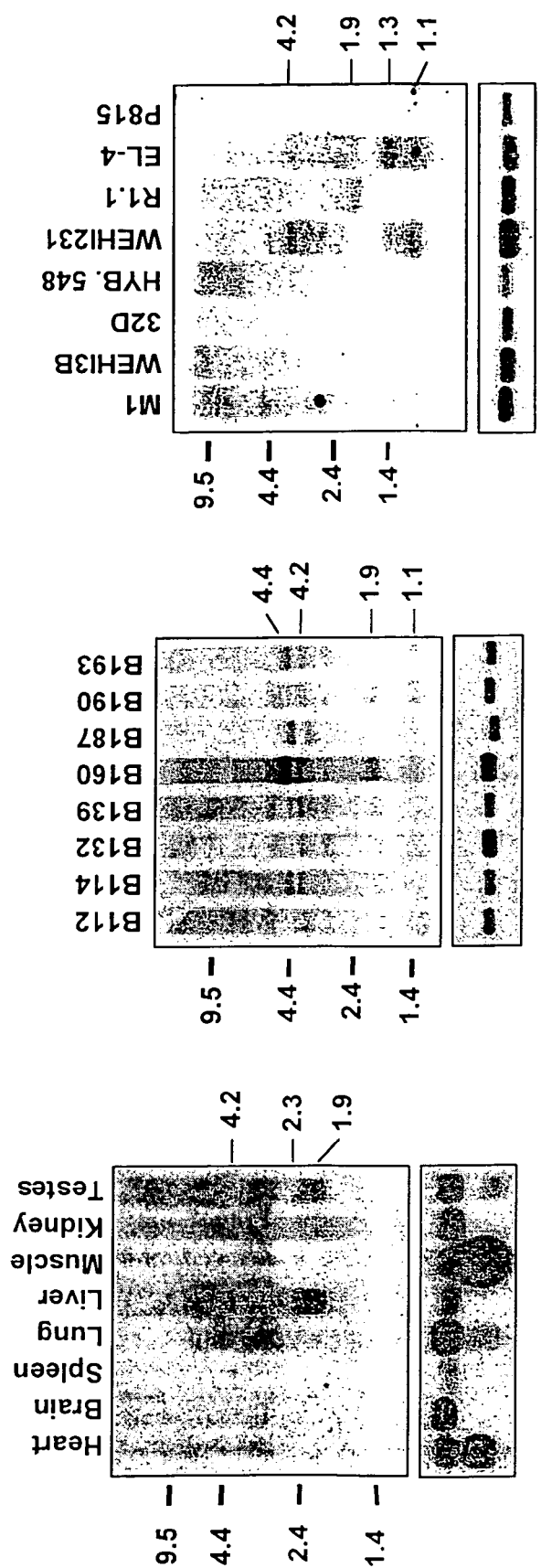
FIGS. 2A-2C show Northern blot analyses of Evi27 expression in murine tissues and cancer cell lines. Multiple tissue Northern blots of normal adult (FIG. 2A), BXH2 leukemic cell lines (FIG. 2B), and various hematopoietic cell lines (FIG. 2C): M1, myeloid leukemia; WEHI3B, monocyte; HYB. 548, B-cell hybridoma; WEHI231, preB-cell lymphoma; R1.1, lymphocytic thymoma; EL4, thymoma, P815, mastocytoma. The blots were also hybridized with a GAPDH or b-actin probe to control for RNA loading. The size in kilobases (kb) of molecular weight markers is show on the left of each panel. To the right of each panel are the sizes of the Evi27 transcripts observed

Northern blot analysis of mouse tissues using both exons as probes confirmed this prediction and showed that the Evi27 hybridization pattern is complex. Six different Evi27 transcripts of approximately 4.4, 4.2, 2.3, 1.9, 1.3, and 10.1 kb in size, could be detected on northern blots (FIGS. 2A-2C). In adult tissues the expression was seen in liver and testes where the 2.3 and 1.9 kb transcripts predominated. Expression of the 4.2 transcript was also seen in liver and testes. In addition, low levels of the 2.3 and 1.9 kb transcripts were seen in kidney (FIG. 2A). With long exposure, the lung showed expression of a 20.1 kb transcript, while the heart showed expression of the 1.3 kb transcript. No expression was seen in skeletal muscle, brain, or spleen.

In addition to adult tissues, Evi27 expression was also detected in some hematopoietic cell lines. These cell lines include the EL-4 T-cell line, which express the 4.2 and 1.3 kb transcripts, the WEHI231 B-cell line which expresses the 4.2, 1.3 and 1.1 kb transcripts, and the R1.1 T-cell line, which expresses the 1.9 kb transcript. In contrast, little or no expression was detected in the 32D, WEHI 3B, and M1 myeloid cell lines, the HYB.548 B-cell line, or the P815 mast cell line (FIG. 2C).

Evi27 expression could also be detected in BXH2 myeloid cell lines whether or not they carry a proviral integration at Evi27. Expression of the 4.4, 4.2, 1.9 and 1.1 kb transcripts was variable among the different lines (FIG. 2C), but the highest expression was seen in the B160 cell line, which contains a viral integration at Evi27. In this cell line the 4.4 kb transcript predominated. These results suggest that viral integration at Evi27 results in increased Evi27 expression.

Figure 3C:
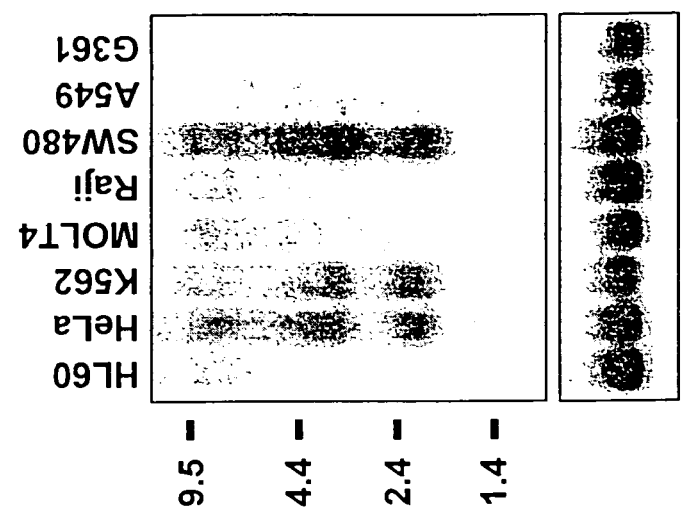
FIGS. 3A-3C show Northern blot analyses of EVI27 expression in human tissues and cancer cell lines. Multiple tissue Northern blots of normal adult (FIG. 3A), immune tissues (FIG. 3B) and cancer cell lines (FIG. 3C) hybridized with an EST specific for the human EVI27 gene. The human cancer cell lines are HL60, promyelocytic leukemia; HeLa, cervical carcinoma; K562, chronic myelogenous leukemia; MOLT4, T-lymphoblastic leukemia; Raji, Burkitt's lymphoma; SW480, colon adenocarcinoma; A549, lung carcinoma; G361, melanoma. The blots were also hybridized with a b-actin probe to control for RNA loading. The size in kb of molecular weight markers is show on the left of each panel.
Figure 3B:
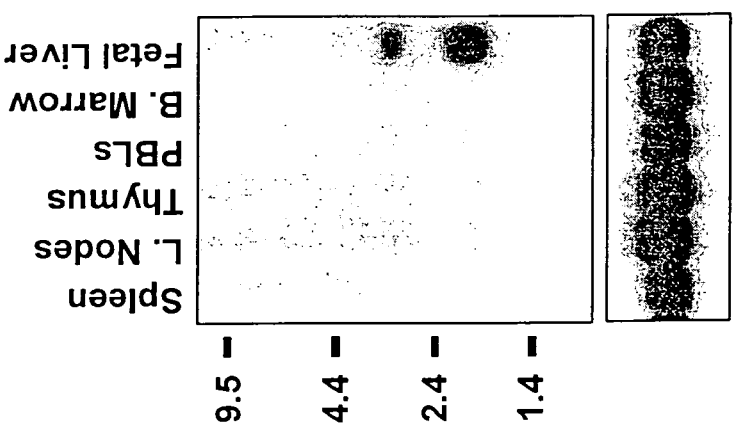
Figure 3A:
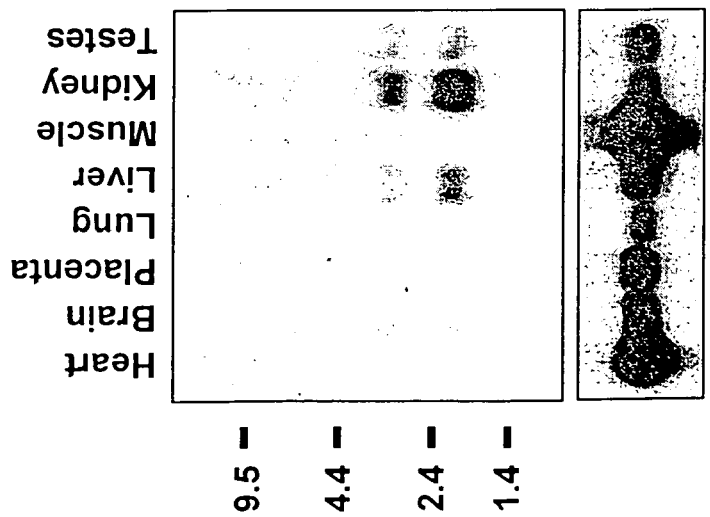

In humans, two EVI27 transcripts, 1.9 kb and 2.7 kb in size, were detected (FIGS. 3A-3C). Human EVI27 expression is therefore considerably less complex than in mouse. The highest EVI27 expression was seen in kidney (FIG. 3A), while in the mouse, Evi27 was expressed at low levels in the kidney. Moderate expression was also observed in the brain, liver, and testes with low to undetectable expression in lung. No EVI27 expression was seen in heart, placenta, and skeletal muscle (FIG. 3A) or in immune tissues such as spleen, lymph nodes, thymus, peripheral blood lymphocytes, or bone marrow (FIG. 3B). High EVI27 expression was, however, observed in the fetal liver.

Within cell lines, moderate EVI27 expression was seen in the cervical carcinoma HeLa, chronic myelogenous leukemia, K562, and colon adenocarcinoma, SW480 cell lines (FIG. 3C), but not in the myeloid leukemia HL-60, acute lymphoblastic T-cell leukemia MOLT-4, Burkitt's lymphoma Raji, lung carcinoma A549 and the melanoma G361 cell lines.

EXAMPLE 15

The Gene Whose Expression is Upregulated by Viral integration at Evi27 Encodes a Novel IL-17 Receptor-Related Protein The complete coding region of human gene was obtained by 3', and then 5' RACE. The primary 5' RACE product using primers from the 3' end of the gene was ~1.9 kb in length, consistent with the size of the major human transcript. A larger minor species was also produced in the 5' RACE reaction. Sequence analysis showed that it contained an additional 950 bp of sequence that was not present in the 1.9 kb product. PCR and genomic sequence analysis showed that this extra sequence was an unspliced intron. Northern analysis showed that the 2.7 kb human transcript contains this unspliced intron and sequence analysis showed that this unspliced intron introduces multiple stop codons into the open reading frame of the protein.

The sequence of the full length 1.9 kb and 2.7 kb transcripts has been deposited in GenBank with accession numbers AF208110 and AF208111, respectively; SEQ. ID NO: 1 and SEQ. ID NO: 2 respectively in the present invention. The predicted uninterrupted protein is 502 amino acids (aa) and has a predicted molecular weight of 56 kD (FIG. 4). pSORT analysis identified a potential cleavable signal peptide at the N terminus of the protein. A putative transmembrane domain starts at residue 293 and ends at residue 309. The cytoplasmic tail is predicted to extend from residue 310 to the C terminus. pSORT analysis also indicated that the protein has type 1a topology. A string of 39 amino acids derived from intronic sequences would be inserted at amino acid 250 in the 2.7 kb transcript. This would result in the synthesis of a 288 amino acids protein with a predicted molecular weight of 31 kD. The transmembrane and cytoplasmic portions of the 502 amino acids isoform are missing in this truncated form of the protein.

Multiple 5' RACE products were also obtained in mouse. Cloning and sequence analysis of these RACE products showed that they can be created by the inclusion of at least two unspliced introns. As in human, these intron sequences introduce multiple stop codons into the open reading frame of the protein. The sequence of the full length 1.9 kb and 2.5 kb mouse transcripts has been deposited in GenBank with accession numbers AF208108 and AF208109, respectively; SEQ. ID NO: 3 and SEQ. ID NO: 4 respectively in the present invention. The mouse 4.4, 4.2, 2.4 and 1.3 kb transcripts have not been cloned and sequenced.

Figure 4:
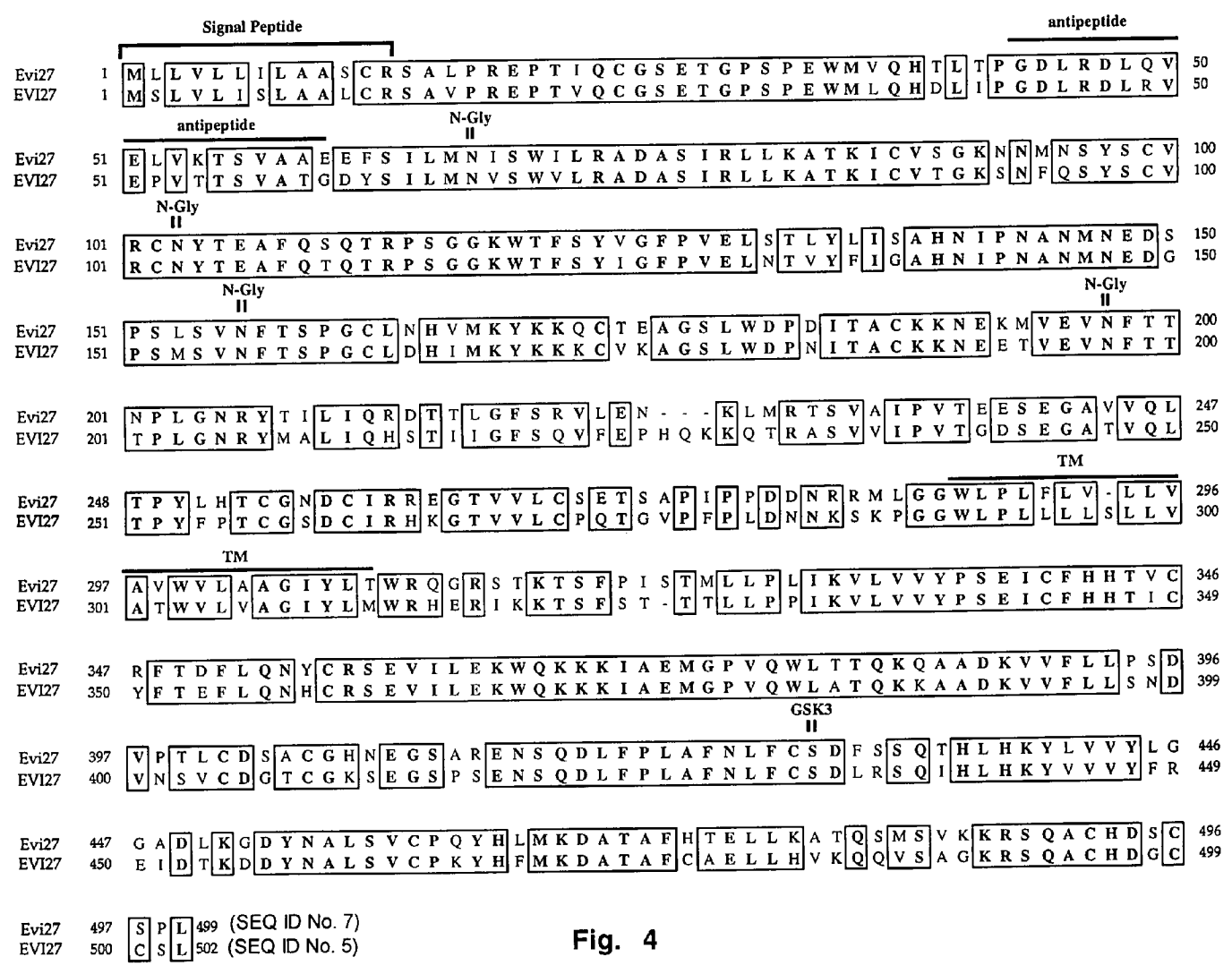
Figure 5:
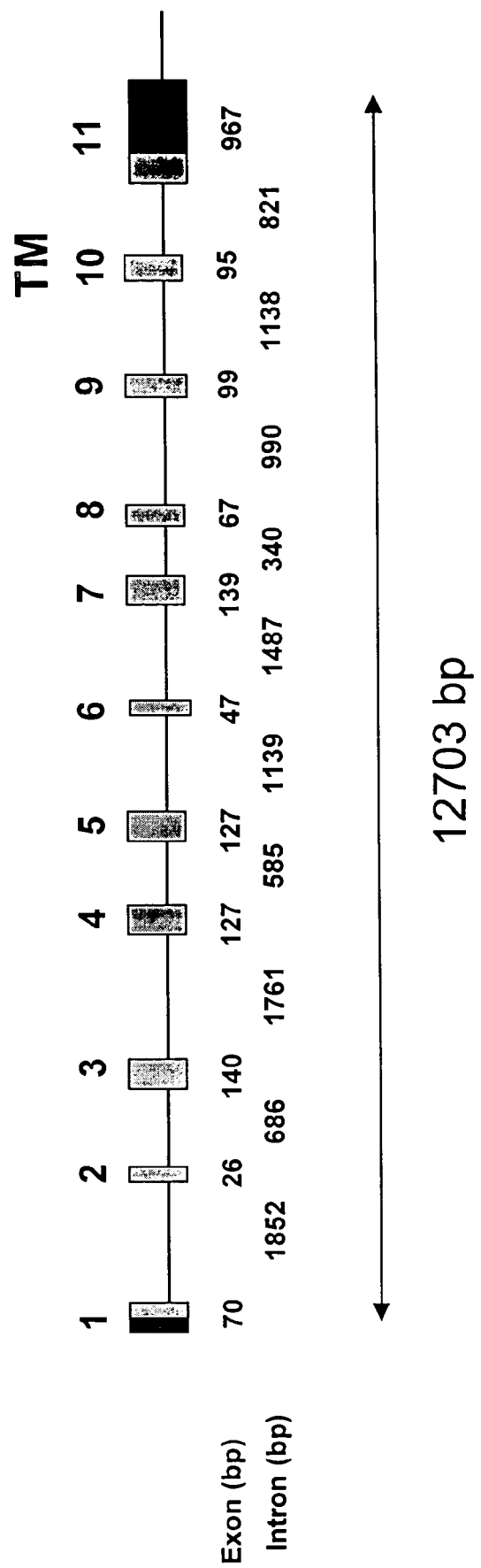
FIG. 5 shows the Evi27 gene structure. The gene consists of 11 exons with the first and last exons containing untranslated regions. The transmembrane domain is located in exon 10.

Genomic sequence analysis indicates that the mouse gene consists of 11 exons and spans ~13 kb of genomic DNA (FIG. 5). It is interesting to note that Evi27 cDNAs specifically lacking exon 10 have been cloned from mouse AML cell lines. The gene is transcribed in the same orientation as the integrated proviruses, which lie in a CpG rich region located approximately 6 kb 5' from the first known exon of the gene (FIG. 1). The predicted open reading frame of the 1.9 kb transcript is 499 amino acids with a predicted molecular weight of 56 kD (FIG. 4). pSORT analysis identified a potential cleavable signal peptide in the N terminus of the protein, just like in the human protein. A putative transmembrane domain starts at amino acid 290 and ends at amino acid 293. The transmembrane domain is located in exon 12 of the gene and is spliced out in variant transcripts sequenced from the WEHI-231 B-cell line. These variant transcripts splice out an exon containing the entire putative transmembrane domain. The lack of this exon does not disrupt the predicted open reading frame of the protein.

In the 2.5 kb transcript, a string of 57 novel amino acids, derived from intron 7, is added at amino acid 162 creating a protein with an open reading frame of 218 amino acids and a predicted molecular weight of 24 kD. Like the shorter human isoform, this isoform would lack the transmembrane and cytoplasmic domains of the protein.

The full-length human and mouse proteins are 83% similar and 76% identical (FIG. 4). The extracellular domain of both proteins contains three conserved N-linked glycosylation and a GSK3 phosphorylation site. A single conserved GSK3 phosphorylation site is also present in the cytoplasmic domain.

Amino acid sequence comparisons showed that Evi27 has significant homology throughout its coding region to the human and mouse IL-17 receptor (IL-17R) (E value=2.5 e-29) (FIGS. 6A-6B). The position of the transmembrane domain with respect to the amino terminus is essentially the same in the two proteins. However, the cytoplasmic tail of the IL-17R is nearly 304 amino acids longer than that of the Evi27. Although Evi27 is predicted to encode both membrane bound and soluble forms, IL-17R is not known to encode a soluble form.

EXAMPLE 16

The Mouse and Human Genes Map in Syntenic Regions

Figure 7A:
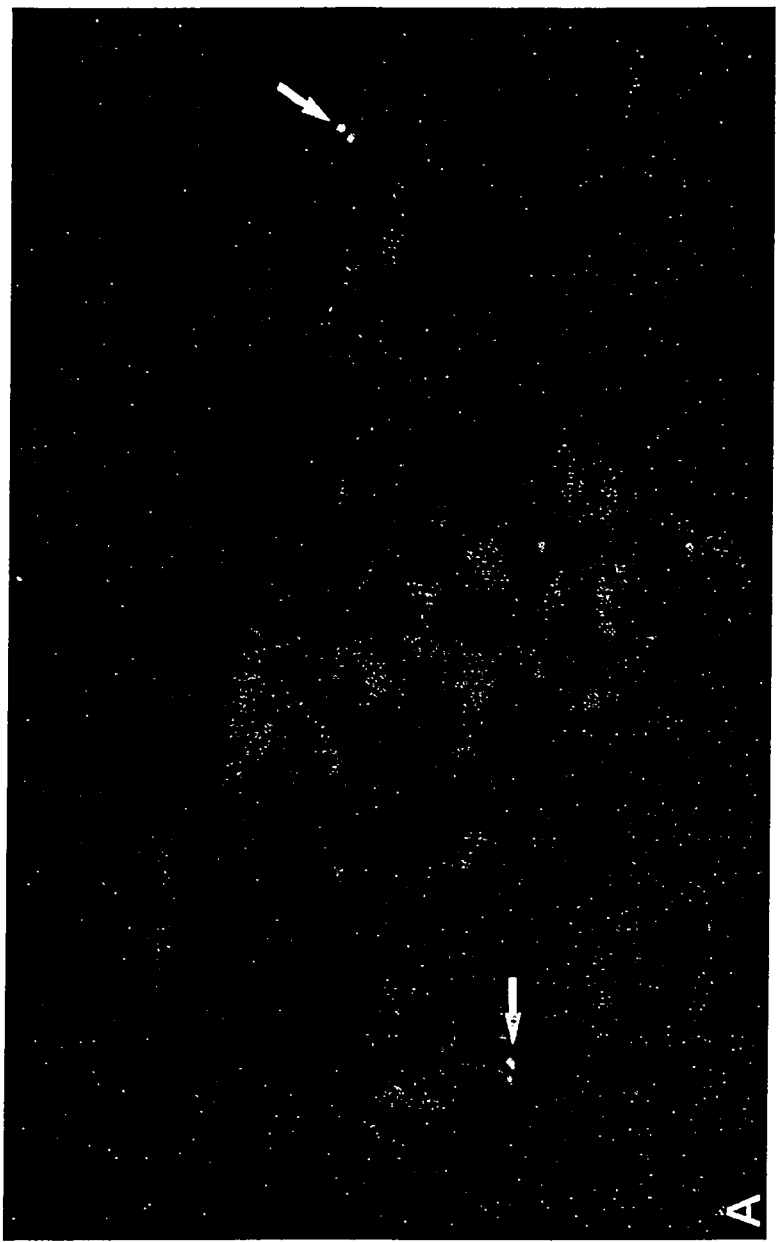
FIG. 7A shows fluorescence in situ hybridization of a PAC clone specific for EVI27 gene to normal human metaphase chromosomes. Arrows indicate localization of the probe.
Figure 7B:
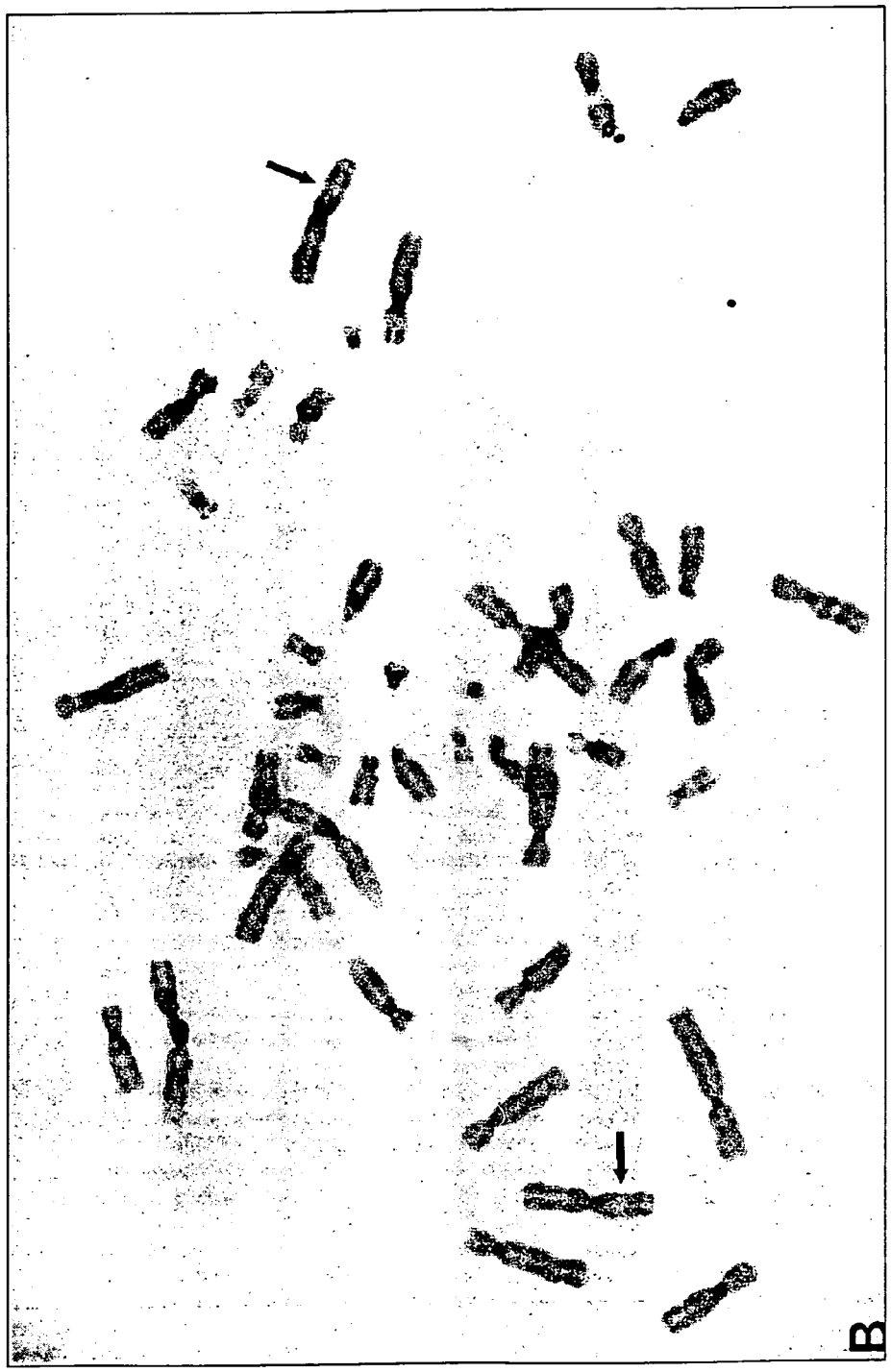
FIG. 7B shows G-banding of the same metaphase spread in FIG. 7A following destaining of FISH reagents. The probe is localized to band 3p21.

The human EVI27 gene was mapped to chromosome 3p21 by fluorescence in situ hybridization of high-resolution G-banded chromosomes (FIGS. 7A-7B). These results are consistent with the mouse mapping data, which localize the mouse gene to chromosome 14 in a region of human 3p21 homology (Copeland et al., 1995). They also confirm that the human gene maps in a region of the human genome that is frequently rearranged in human myeloid leukemia.

EXAMPLE 17

Expression and Subcellular Localization of Evi27

The expression and subcellular localization of the mouse protein was examined using a polyclonal antibody raised against a peptide derived from the C-terminus of Evi27. Antibody specificity was confirmed by immunofluorescence staining of 32D cells, which express undetectable levels of Evi27 mRNA (FIG. 8A), and 32D cells stably transfected with a 2.7 kb Evi27 cDNA clone. Western blot analysis showed that whereas the parental 32D cells show weak expression of the expected 55 kD full length protein, the transfected line expresses approximately 3-5 fold higher levels of this isoform (FIG. 8B). Immunofluorescence analysis showed weak staining in the parental 32D cells whereas the transfected cells show very abundant staining on the surface with a capping pattern (FIG. 8C, left panels). Surface expression of Evi27 was further shown by flow activated cell sorting analysis (FIG. 8D). Clear cell surface staining was observed after analysis of live cells or fixed, but not permeabilized, transfected cells (data not shown). In all experiments the staining could be quenched by preincubation of the antisera with Evi27 peptide (FIG. 8C, right panels and FIG. 8D), thus indicating the antiserum is specific for Evi27.

Figure 9:
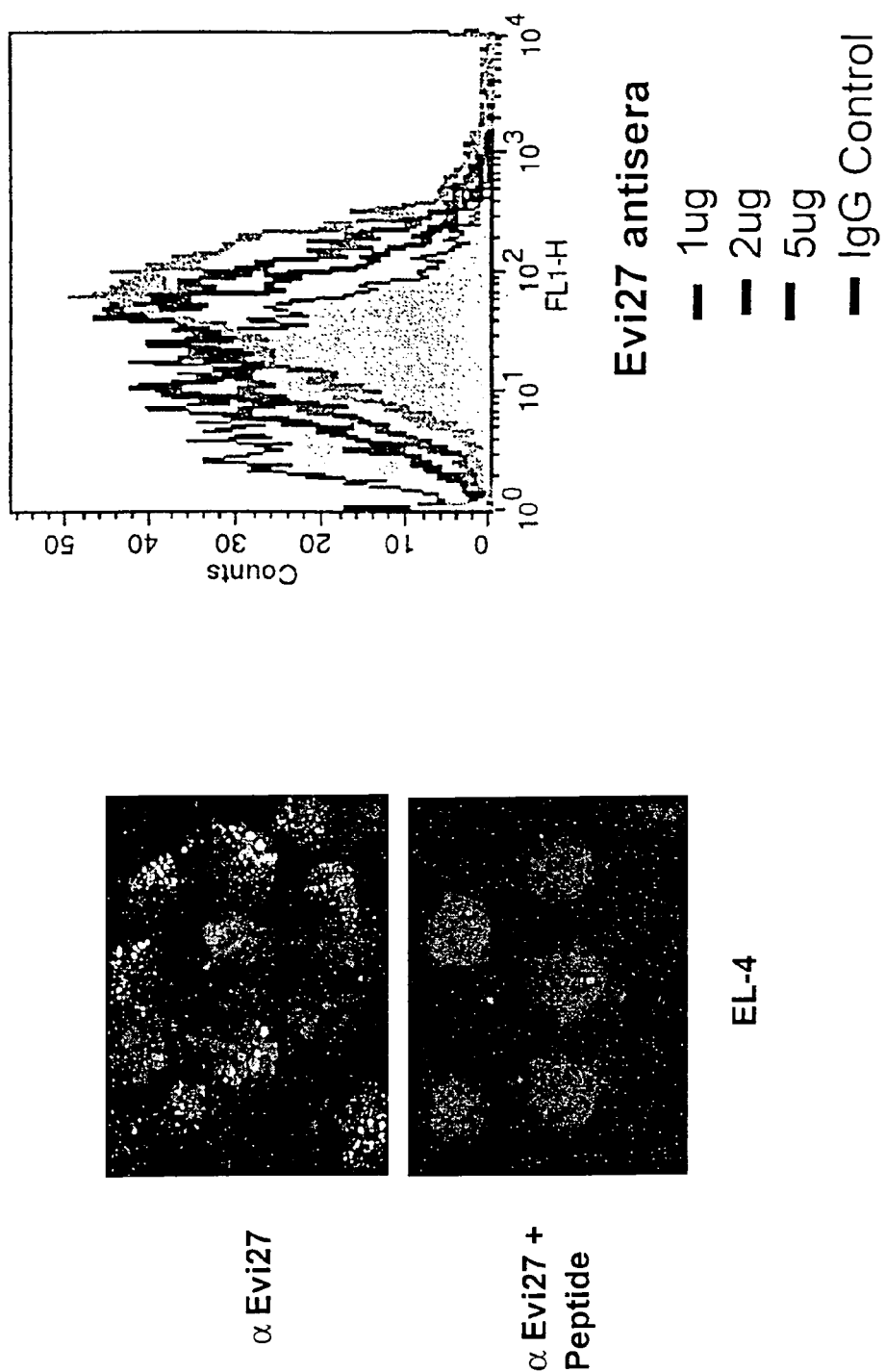
FIG. 9 shows cell surface expression and capping of Evi27 on murine T cell lymphoma EL-4. The left panel shows immunochemistry of the EL-4 cells with the anti-Evi27 antibody before and after pre-treatment with Evi27 peptide. Right panel shows FACs analysis with increasing amount of anti-Evi27 antibody. The capping of Evi27 possibly indicates polydimerization and receptor activation of Evi27.
Figure 10:
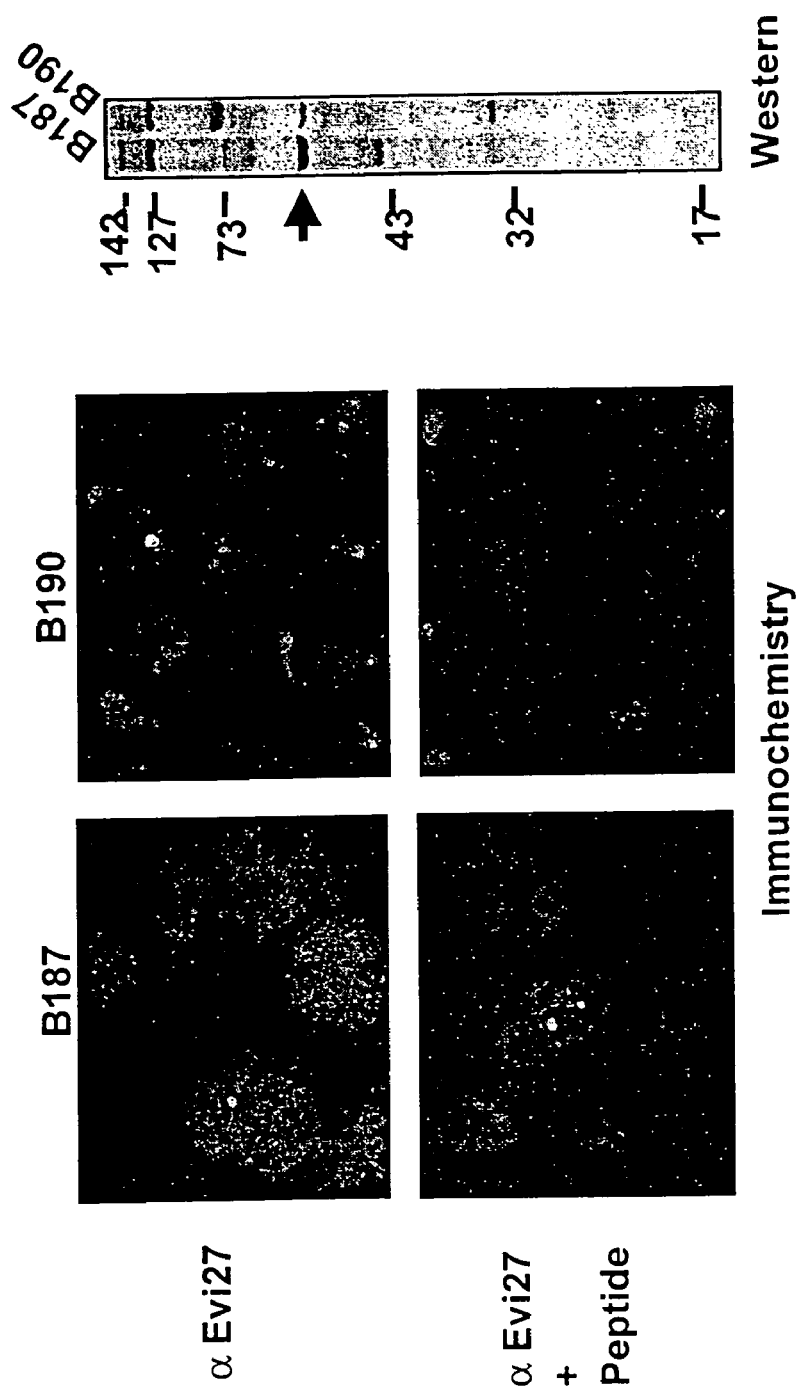
FIG. 10 shows subcellular localization of Evi27 in myeloid leukemia B187 and B190. The left panel shows immunochemistry of the B187 and B190 cells with the anti-Evi27 antibody before and after pre-treatment with Evi27 peptide. B187 cells show diffuse speckled staining in the cytoplasm, whereas B190 cells shows a capping pattern similar to the EL-4 cells. The signals could be competed away by preincubation with Evi27 peptide. Right panel shows western blot analysis of same cell lines with anti-Evi27. Both cell lines express multiple isoforms of Evi27, and B 187 cells express more of the 55 kD isoform. The bands could be competed away by preincubation with Evi27 peptide.

Murine T cell lymphoma EL-4 cells also express Evi27 on cell surface and the cell surface capping possibly indicates polydimerization and receptor activation of Evi27 (FIG. 9). In contrast, Evi27 shows different localization in murine AML cells. Myeloid leukemia cells B187 and B160 both show diffuse speckled staining pattern in the cytoplasm, whereas the B190 cells show a capping pattern similar to the T cell lymphoma EL-4 (FIGS. 10-11). Moreover, abundant Evi27 protein was found in the cytoplasm, but not on the cell surface, of the B160 cells (FIG. 11).

EXAMPLE 18

Western Blot Analysis of Evi27 Protein Expression

Figure 12B:
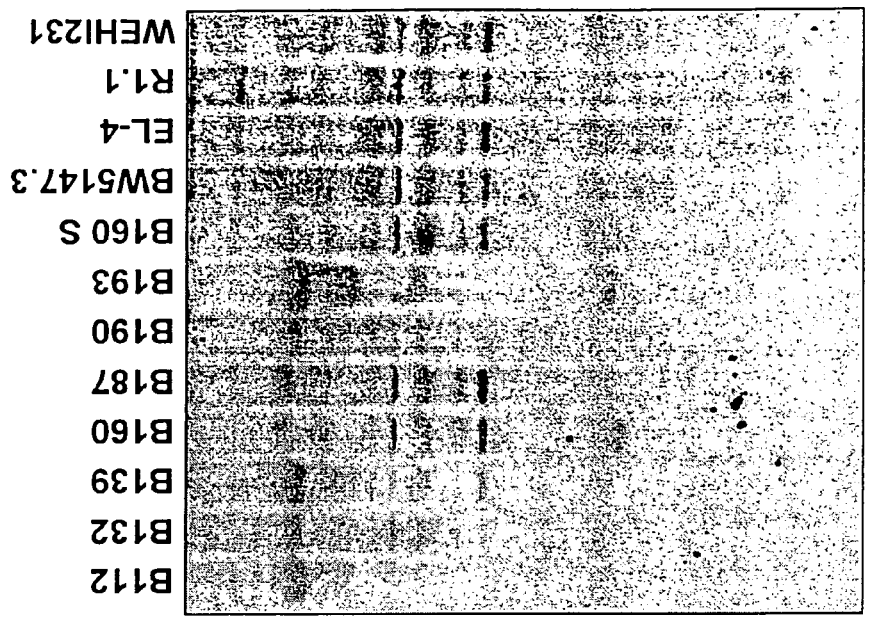
FIGS. 12A-12B show Western blot analysis of Evi27 protein expression in BXH2 leukemia cell lines, EL4 and R1.1 T-cell lines, and the WEHI231 B-cell line. 10 mg of protein from cell lysates was run in tandem and hybridized with Evi27 antibody either without (FIG. 12A) or with (FIG. 12B) preincubation with Evi27 peptide. Note the absence or reduction of specific bands in panel (FIG. 12B) compared to (FIG. 12A). Molecular weight standards in kD are indicated to the left. The Evi27 isoforms and sizes are indicated to the right of panel A.
Figure 12A:
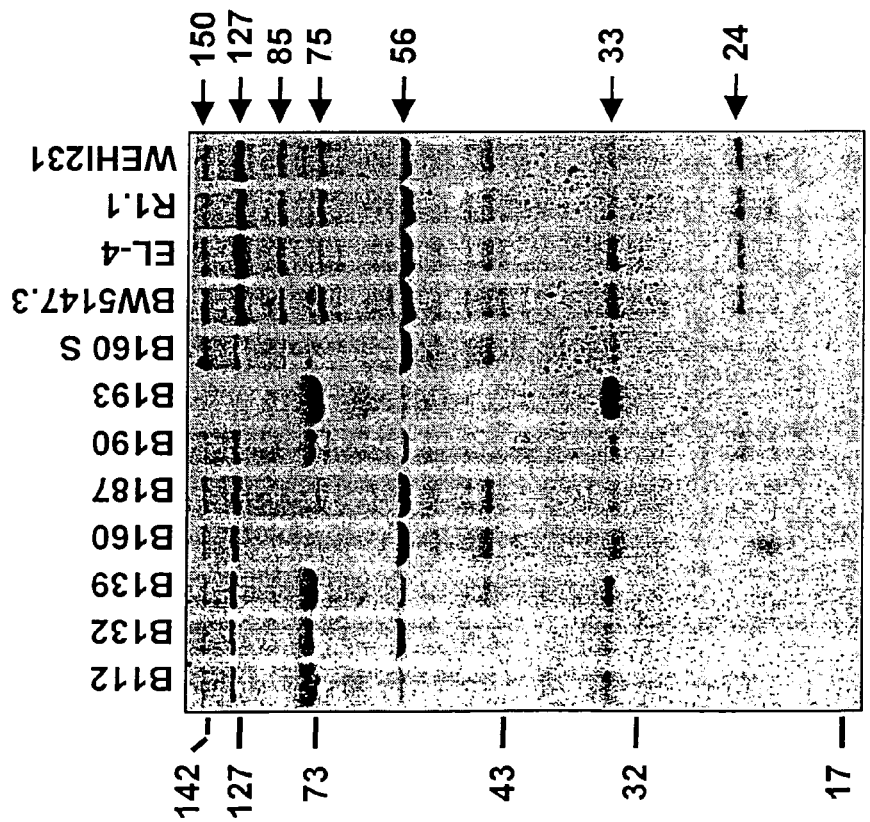

Western blot analysis of a number of leukemia cell lines confirmed the Northern results and showed that many different Evi27 isoforms are expressed at the protein level (FIGS. 12A-12B). A 56 kD protein, which is the predicted size of the full length protein containing the transmembrane and cytoplasmic domains, was expressed in most samples tested (FIG. 12A). The EL4 and R1.1 T-cell lines and the WEHI 231 B-cell line also express a 24 kD protein, which is the predicted size of the truncated protein resulting from intron incorporation and an 85 kD protein (FIG. 12A). This protein is also expressed at low levels in the B190 cell line but not in the other the BXH2 leukemia cell lines tested.

Several cytokine receptors also produce soluble forms of the receptor by proteolytic cleavage of the membrane bound receptor. The cleavage sites are located near the plasma membrane in the extracellular domain of the receptor. Proteolytic cleavage of the Evi27 membrane receptor in this region is predicted to produce a 33 kD protein. A band of this size is also present in most samples tested (FIG. 12A). Several unexpected sized Evi27 bands were also detected on the Western blot. These protein bands can all be competed away by the addition of Evi27 peptide (FIG. 12B), indicating that they contain authentic Evi27 protein sequences.

The origin of these protein bands is unknown but could result from the translation of Evi27 mRNA transcripts that have yet to be sequenced or may be indicative of homo- or heteropolymer formation. The expression of these protein bands is sometimes variable. For example, the 75 kD band is expressed at low or undetectable levels in the B160 and B187 cell lines. The B193 cell lines does not express the 150 kD and 127 kD bands, but does expresses high levels of the 75 and 33 kD bands. The reason for this is not clear, but may reflect the differentiation state of the cell line. Consistent with this hypothesis, T- and B-cell lines express Evi27 protein bands that are not expressed in BXH2 myeloid cell lines (i.e., 24 and 85 kD bands).

Figure 13:
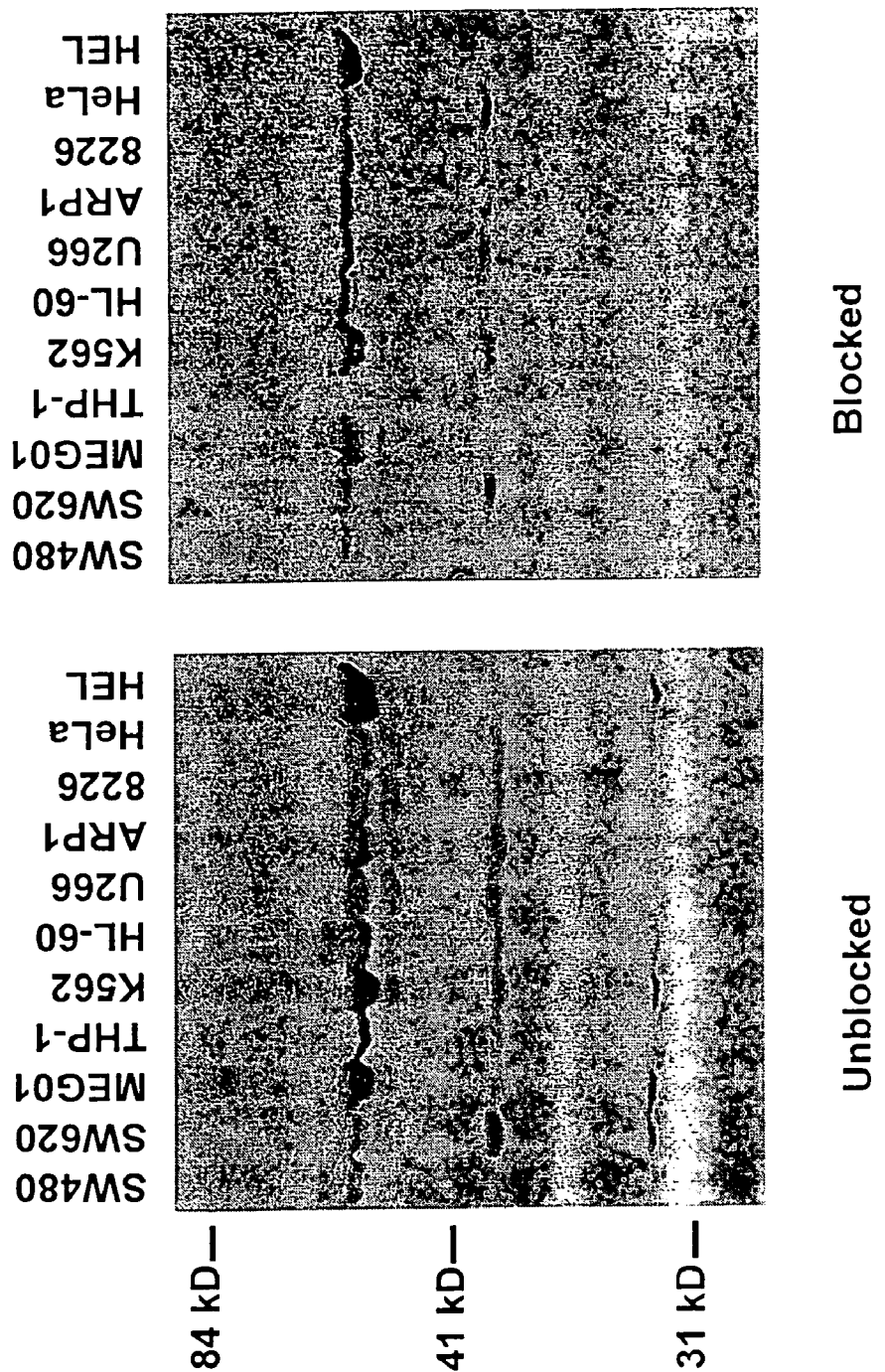
FIG. 13 shows western blot analysis of Evi27 expression in human cell lines. SW480 and SW620 are colon adenocarcinoma: MEG01, megakaryocytic leukemia; THP-1, monocytic leukemia; K562, chronic myelogenous leukemia; HL-60, promyelocytic leukemia; U266, ARP1 and 8226, multiple myeloma; HeLa, cervical carcinoma; HEL, erythrocytic leukemia. 55 kD and 30 kD are major bands recognized, thus the antibody recognizes both human Evi27 protein isoforms. The bands could be competed away by preincubation of Evi27 antisera with Evi27 peptide as shown in the right panel. MEG01, K562 and HEL cell lines express the highest levels of the Evi27 protein.
Figure 14:
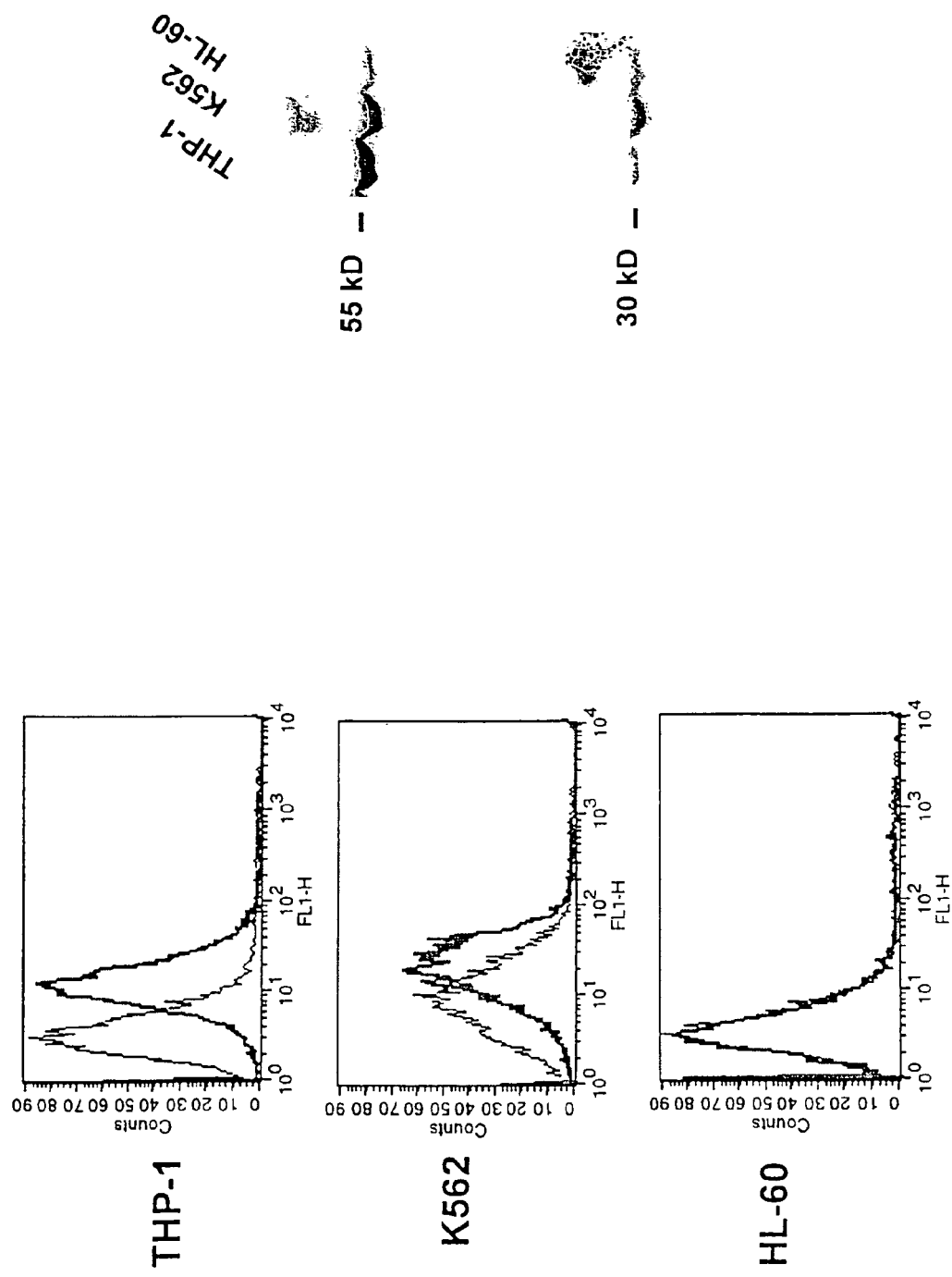
FIG. 14 shows surface expression of Evi27 on human hematopoietic cell lines. Left panel shows FACs analysis of Evi27 expression on the surface of various human cell lines (red: affinity purified anti-Evi27 antisera; black: IgG control). Evi27 was expressed on THP-1 and K562 cells but not the HL-60 cells. Right panel shows western blot analysis of same cell lines with anti-Evi27. As expected from the FACs data, THP-1 cells express more Evi27 protein than K562 cells, which in turn express more Evi27 than HL-60 cells. It is also shown that K562 cells produce more of the 30 kD soluble form of the Evi27 protein.

Evi27 expression was also examined in human hematopoietic cells. Western blot analysis showed that MEG01 (megakaryocytic leukemia), K562 (chronic myelogenous leukemia) and HEL (erythrocytic leukemia) cell lines express the highest levels of Evi27 protein (FIG. 13). Flow activated cell sorting analysis indicated that there is high level of surface expression on THP-1 (monocytic leukemia) and K562 cells but not on HL-60 (promyelocytic leukemia) cells (FIG. 14).

Discussion

The studies described here show that retroviral integration at the Evi27 locus in BXH2 murine myeloid leukemias results in the increased expression of a novel gene with homology to the IL-17 receptor. A number of cytokine receptors (i.e., v-mpl or Tpor, Il6ra, Epor, Il9r, Csf1, Il2ra, Il4ra, and Ifngr2) or their ligands (i.e., Il6, Csf1, Il3) are reported targets of retroviral integration or transduction in mouse leukemia/lymphomas making cytokines/cytokine receptors one of the largest and most important classes of leukemia genes (Ymer et al., 1985; Wendling et al., 1986; Penciolelli et al., 1987; Gisselbrecht et al., 1987; Sugita et al., 1990; Blankenstein et al., 1990; Souyri et al., 1990; Hino et al., 1991; Chretian et al., 1994; Flubacher et al., 1994; Li et al., 1999). The Evi27-encoded cytokine-related receptor is therefore an excellent candidate for a new leukemia disease gene.

The human EVI27 gene was also cloned and mapped to chromosome 3p14-p21, in a region syntenic to the mouse gene. The human protein is 76% identical to the mouse protein at the amino acid level. This is somewhat higher than the recently described homology between the mouse and human IL-17 receptors, which are 69% identical at the amino acid level (Yao et al., 1997). This conservation suggests that Evi27 receptor function is evolutionarily conserved between human and mouse.

Proviral integrations at Evi27 are located about 6 kb upstream from the IL-17 receptor-related gene and result in increased gene expression. Viral integration at Evi27 may thus induce disease simply by upregulating receptor expression. However, given the complex expression pattern observed for Evi27, it is also possible the viral integration induces disease by altering Evi27 isoform expression. In the mouse, as many as six Evi27 transcripts are detected on Northern blots. Two of the transcripts result from intron incorporation and are predicted to produce a truncated soluble form of the receptor lacking the transmembrane and cytoplasmic domains. Several cytokine receptors are known to produce soluble as well as membrane bound forms and it is now well documented that the soluble receptors can have both positive and negative effects on ligand signaling (for review see Heaney and Golde, 1996). The origin of the other Evi27 transcripts has not been determined. It is thus possible that one or more of these uncharacterized messages encode sequences that are located upstream of Evi27 proviral integration sites at Evi27. If this is the case, then Evi27 proviral integrations may prevent these messages from being expressed and this may have important disease consequences.

IL-17r/Evi27 are unusual in that they have no homology with any protein in public databases, including other cytokine receptor proteins, and they have no recognizable motifs associated with intracellular signalling (Yao et al., 1995b). Many disease-related cytokine receptors involved in leukemogenesis contain kinase domains; however, it is not unprecedented to find receptors lacking kinase domains that are involved in disease. For example, the human MAS1 oncogene, which encodes a functional angiotensin receptor, is a G-protein coupled receptor that functions through phosphatidylinositol 4,5-bisphosphate hydrolysis (Young et al., 1986; Jackson et al., 1988). Evi27 may thus identify a new disease pathway.

At least seven different Evi27 isoforms (i.e., 24, 33, 56, 47, 75, 127, and 150 kD in size) were also detected in BXH2 leukemia cell extracts by western analysis using an Evi27-specific antibody. All leukemia extracts expressed the 56 kD isoform (the membrane bound receptor) as well as the 33 kD isoform (a postulated proteolytic cleavage containing the extracellular ligand-binding domain of the receptor). Expression of the other isoforms was variable among the extracts. One of seven cell extracts (B190) expressed the 24 kD isoform (a putative truncated receptor resulting from intron incorporation), three extracts (B139, B160, and B187) express the 47 kD isoform, five extracts (B112, B132, B139, B190, B193) the 75 kD isoform, and six extracts (B112, B132, B139, B160, B187, B190) the 150 kD isoform. The origin of these larger isoforms (i.e., oligomerization) or the reason for their variable expression (i.e. differentiation state of the cell) is presently unclear.

Only one BXH2 leukemia cell extract, B160, analyzed on Western blots is known to contain a proviral integration at Evi27. The 56 kD isoform is overexpressed in B160 cells, consistent with Northern results showing that viral integration at Evi27 results in increased Evi27 expression. Surprisingly, the 56 kD isoform is also overexpressed in B187 cells, which are not known to carry a viral integration at Evi27. Perhaps, B187 cells harbor a viral integration at Evi27 that maps outside the region examined on Southern blots or there are other mechanisms for upregulating expression of this isoform other than proviral integration. It is interesting to note that B187 cells, like B160 cells, also fail to express the 75 kD isoform. One intriguing possibility is that viral integration at Evi27 blocks expression of this isoform.

Evi27 expression is restricted in the hematopoietic cells. Northern analysis showed that Evi27 is expressed in T cells and ESTs homologous to the mouse gene have been identified in CD4$^+$ T-cells. Likewise, the mouse preB-cell line WEHI231 expresses Evi27 and ESTs homologous to EVI27 have been identified in human germinal center B cells. No Evi27 expression was seen in the late stage B-cell line 548, the Burkitt lymphoma cell line Raji, the murine erythroid line D1b, or the mast cell line P815. A complex pattern of expression was observed within the myeloid compartment. Variable expression was seen in BXH2 leukemia cells, while little or no Evi27 expression was seen in the M1 and 32D murine myeloid leukemia cell lines or in the monocytic leukemia cell line WEHI-3B. Evi27 is expressed, however, in the chronic human myelogenous leukemia cell line K562, but not in the promyelocytic leukemia cell line HL-60. These results suggest that Evi27 expression may be tightly regulated during myeloid cell differentiation and imply that Evi27 may have an important function in controlling the growth and/or differentiation of hematopoietic cells. Proviral integration at Evi27 may interfere with this function(s) and, in doing so, lead to myeloid disease.

The Evi27 subcellular protein distribution was also analyzed in various mouse hematopoietic cell lines. In the EL4 T-cell and WEHI231 B-cell lines, Evi27 protein was largely found on the cell surface in a capping pattern. Interestingly, only one BXH2 leukemia cell line, B190, has a similar staining pattern. In the other BXH2 leukemia cell lines examined, including B160, which has a proviral integration at Evi27, Evi27 protein is distributed throughout the cytoplasmic where it exhibits a punctate staining pattern. Western blot analysis shows that cells exhibiting the ER/Golgi staining pattern uniquely express the 24 kD Evi27 isoform. It is possible that the 24 kD isoform uniquely localizes to the ER/Golgi and somehow prevents the other Evi27 isoforms from entering the cytoplasm. Alternatively, it is possible that a cofactor or heterodimeric partner required for transport from the ER/Golgi complex is differentially expressed. This hypothesis is strengthened by the fact that the 32D cell line transfected with the 56 kD isoform still lacks the cytoplasmic distribution seen in B160 or B187. In support of this possible mechanism, the expression of beta-2-microglobulin is required for cell surface expression of MHC class I or class I-like molecules (Lamouse-Smith et al., 1993; Feder et al., 1998). Additionally, the receptor-associated protein (RAP), a type of chaperone, is especially designed to assist in the biosynthesis and intracellular transport of endocytic receptors (Willnow, 1998) and band 3 (AE1 gene) plays a chaperone-like role required for the recruitment of Glycophorin A to the red blood cell plasma membrane (Hassoun et al., 1998). Finally, recent studies have shown that calnexin and Ig-alpha/Ig-beta interactions with membrane immunoglobulins are critical for the surface expression of the B cell antigen receptor of the IgM and IgD classes (Wu et al., 1997).

IL-17 (CTLA8) is a homodimeric cytokine of about 32 kD expressed exclusively from human memory T cells or mouse alpha beta TCR$^+$CD4$^-$CD8$^-$ thymocytes (Rouvier et al., 1993; Yao et al 1995a; Yao et al., 1995b; Kennedy et al., 1996). In contrast with the tightly controlled expression of the ligand, the IL-17 receptor is ubiquitously distributed but more abundant in spleen and kidney (Yao et al., 1995b). Although devoid of direct effects on cells of hematopoietic origin, IL-17 induces the secretion of IL-6, IL-8, PGE2, MCP1 and G-CSF by adherent cells like fibroblasts, keratinocytes, epithelial and endothelial cells (Yao et al., 1995a; Yao et al., 1995b; Fossiez et al., 1996). When cultured in the presence of IL-17, fibroblasts can sustain the proliferation of CD34$^+$ human progenitors and their preferential differentiation into neutrophils (Fossiez et al., 1996). Adenovirus-mediated transfer of murine IL-17 cDNA into liver has also been shown to induce a transient, but dramatic granulopoiesis in vivo, except in IL-6-deficient mice (Schwarzenberger et al., 1998).

The Evi27 protein is a member of the IL-17 receptor family. Two new members of the IL-17 cytokine family have recently been identified and these studies have demonstrated that IL-17B and IL-17C do not bind the IL-17 receptor extracellular domain, indicating that IL-17B and IL-17C are likely to bind unique, yet uncharacterized receptors (Li et al., 2000). In a survey of cytokine induction, IL-17B and IL-17C stimulate the release of TNF-a and IL-1b from the monocytic leukemia cell line THP-1 (Li et al., 2000). RT-PCR analysis has shown that IL-17B is expressed by both the B160 leukemia and the stromal cell on which it depends. It is speculated that Evi27 may represent the receptor for IL-17B or IL017C. Based on these data a model for Evi27 in myeloid leukemia development is proposed. Terminal differentiation of myelomonocytic precursor cells likely result in the down regulation of Evi27 expression. However, proviral insertions at Evi27 result in constitutive expression of the receptor. Binding of IL-17B/C to the Evi27 receptor would trigger the release of TNF-a and the IL-1b by the leukemic cells. The TNF-a and IL-1b would in turn provoke the production of multilinage hematopoietic growth factors, adhesion molecules, and inflammatory cytokines by stromal cells (Bagby, 1994). These stromal cell derived factors then support the growth and survival of the leukemia cell and may account for the absolute dependence of the B160 leukemia on the stromal feeder layer for growth and survival.

The human homologue of Evi27 may also be involved in human disease. EVI27 maps to chromosome 3p21, a region consistently deleted in a variety of human cancers. Loss of 3p heterozygosity is also frequently observed in renal cell carcinoma, lung cancer and breast cancer and analysis of 3p allele loss in renal cell cancer has localized a candidate tumor suppressor gene to 3p21 (van den Berg et al., 1997). These results are consistent with the hypothesis that chromosome 3p encodes a number of tumor suppressor genes. Given that EVI27 maps to 3p21 and is expressed at high levels in normal human kidney, it will be interesting to determine whether this gene is affected by 3p21 mutations in renal cell carcinoma. EVI27 also may be a human myeloid leukemia disease gene. Recurrent treatment-related chromosome 3p21 breaks are frequently observed in myelodysplastic syndrome and acute myeloid leukemia patients (Shi et al., 1996), and 3p21 is the most frequently deleted region in human CML (Johansson et al., 1997). Future studies will be aimed at determining whether EVI27 is a human myeloid leukemia disease gene.

An Evi27 ligand, IL-17E, that induces activation of NF-kB and stimulates production of the proinflammatory chemokine IL-8 was identified recently. Together with the restricted expression of Evi27 disclosed herein, it is likely that Evi27 mediates the secretion of proinflammatory cytokines such as IL-8 and plays important role in the developmental and/or disease processes of hematopoietic cells. Hence, modulating the expression of Evi27 at the RNA or protein level may be exploited for use in the treatment of diseases such as cancer or autoimmune diseases. A number of methods can be used to modulate Evi27 expression, e.g. by anti-sense oligonucleotides, small molecules that bind to the receptor, modified IL-17E ligand that may stimulate or repress the activity of the Evi27 receptor, and the use of soluble form of the Evi27 receptor.

The following references were cited herein:

Bagby (1994). *The Molecular Basis of Blood Diseases.* Stamatoyannopoulos G, Nienhuis A. W., Majerus P. W. and Varmus H. (eds). W. B. Saunders Press: Philadelphia, p. 71-106.
Baumbach et al., (1988). *J. Virol.,* 62, 3151-5
Bedigian et al., (1984). *J. Virol.,* 51, 586-594.
Benton et al., (1977). *Science,* 196, 180-2.
Blankenstein et al., (1990). *J. Exp. Med.,* 171, 965-70
Buchburg et al., (1990) *Mol. Cell. Biol.,* 10, 4658-4666.
Chretien et al., (1994). *Blood,* 83, 1813-1821
Copeland et al., (1993). *Science,* 262, 57-66.
Copeland N G, Jenkins N A 1999. Myeloid leukemia: disease genes and mouse models. In Animal Models of Cancer Predisposition Syndromes (eds Hiai, H. & Hino, O.) 53-63 (Karger, Basel, 1999).
Feder et al., (1998). *Proc Natl Acad Sci USA.,* 95, 1472-7.
Flubacher et al., (1994) *J. Virol.,* 68, 7709-16
Fossiez et al., (1996). *J. Exp. Med.,* 183, 2593-603.
Gilbert et al., (1993). *J. Virol.,* 67, 2083-90.
Hassoun et al., (1998). *Blood* 91, 2146-51.
Heaney et al., (1996). *Blood,* 87, 847-57
Hino et al., (1991). *Mol. Cell. Biol.,* 11, 5527-33.
Jackson et al., (1988). *Nature* 335, 437-40
Jenkins et al., (1982). *J. Virol.,* 42, 379-388.
Johansson et al., (1997). *Leukemia,* 11, 1207-13.
Kennedy et al., (1996) *J. Interferon Cytokine Res.,* 16, 611-617.
Lamouse-Smith et al., (1993). *J. Immunol.,* 15, 6283-90.
Largaespada et al., (1995). *J. Virol.,* 69, 5095-5102.
Li et al., (1999). *Nat. Genet.,* 23, 348-353.
Li et al., (2000). *Proc. Natl. Acad. Sci. USA,* 97, 773-778.
Liao et al., (1997). *Oncogene,* 14, 1023-9.
Look A T. (1997). *Science,* 278, 1059-64.
Lupas, et al., (1991). *Science,* 252, 1162-1164.
Morishita et al., (1988). *Cell,* 54,831-40
Nakai et al., (1992). *Genomics,* 14, 897-911.
Nakamura, et al., (1996a) *Nat. Genet.* 12, 149-153.
Nakamura, et al., (1996b). *Nat. Genet.,* 12, 154-158.
Ogawa et al., (1996). *Oncogene,* 13, 183-91.
Roberts et al., (1998). *Hum. Mol. Genet.,* 7, 1169-78
Rouvier et al., (1993). *J Immunol* 150, 5445-56.
Sambrook et al., *Molecular Cloning, A Laboratory Manual* 2nd edn. (Cold Spring Harbor, Laboratory Press New York, 1989).
Schwarzenberger et al., (1998). *J. Immunol.,* 161, 6383-9.
Shaughnessy et al., (1999). *Oncogene,* 18, 2069-84.
Shi et al., (1996). *Cytogenet. Cell Genet.,* 74, 295-9
Sugita et al., T. (1990). *J. Exp. Med.,* 171, 2001-9.
Viskochil et al., (1990). *Cell,* 62, 187-92.
van den Berg et al., (1997) *Genes Chromosomes Cancer,* 19, 228-32.
Willnow T E. (1998). *Biol. Chem.,* 379, 1025-31.
Wu Y, Pun C, Hozumi N. (1997). *Immunol.,* 158, 2762-70.
Yao et al., (1995a). *Immunity,* 3, 811-821.
Yao et al., (1995b). *J. Immunol.,* 155, 5483-6
Yao et al., (1997). *Cytokine,* 9, 794-800
Young et al., (1986). *Cell,* 45, 711-9.
Ymer et al., (1985). *Nature,* 317, 255-8.

Any patents or publications mentioned in this specification are indicative of the levels of those skilled in the art to which the invention pertains. Further, these patents and publications are incorporated by reference herein to the same extent as if each individual publication was specifically and individually indicated to be incorporated by reference.

One skilled in the art will appreciate readily that the present invention is well adapted to carry out the objects and obtain the ends and advantages mentioned, as well as those objects, ends and advantages inherent herein. The present examples, along with the methods, procedures, treatments, molecules, and specific compounds described herein are presently representative of preferred embodiments, are exemplary, and are not intended as limitations on the scope of the invention. Changes therein and other uses will occur to those skilled in the art which are encompassed within the spirit of the invention as defined by the scope of the claims.

What is claimed is:

1. A method of inhibiting the biological activity of an IL-17 receptor-related protein, Evi27, in a cell expressing the Evi27 on the cell surface, comprising contacting the cell with a soluble isoform of the Evi27 protein encoded by the nucleic acid of SEQ ID NO:3, in the presence of Evi27 ligand (IL-17E), wherein said soluble protein is about 33 or 56 kD in size as detected by western blot analysis of BXH2 leukemia cells, and said soluble protein binds to Evi27 ligand thereby decreasing the biological activity of the Evi27.

2. The method of claim 1, wherein the soluble protein is about 33 kD in size.

3. The method of claim 1, wherein said Evi27 biological activity is secretion of a cytokine.

4. The method of claim 3, wherein said cytokine is IL-8.

5. The method of claim 1, wherein the cell is hematopoletic cell or a leukemia cell.

* * * * *

SEQUENCE LISTING

<160> NUMBER OF SEQ ID NOS: 9

<210> SEQ ID NO 1
<211> LENGTH: 1827
<212> TYPE: DNA
<213> ORGANISM: Homo sapiens
<220> FEATURE:
<221> NAME/KEY: prim_transcript
<223> OTHER INFORMATION: cDNA of human Evi27

<400> SEQUENCE: 1

| | | | | | |
|---|---|---|---|---|---|
| cggcgatgtc | gctcgtgctg | ataagcctgg | ccgcgctgtg | caggagcgcc | 50 |
| gtaccccgag | agccgaccgt | tcaatgtggc | tctgaaactg | ggccatctcc | 100 |
| agagtggatg | ctacaacatg | atctaatccc | cggagacttg | agggacctcc | 150 |
| gagtagaacc | tgttacaact | agtgttgcaa | caggggacta | ttcaattttg | 200 |
| atgaatgtaa | gctgggtact | ccgggcagat | gccagcatcc | gcttgttgaa | 250 |
| ggccaccaag | atttgtgtga | cgggcaaaag | caacttccag | tcctacagct | 300 |
| gtgtgaggtg | caattacaca | gaggccttcc | agactcagac | cagaccctct | 350 |
| ggtggtaaat | ggacattttc | ctatatcggc | ttccctgtag | agctgaacac | 400 |
| agtctatttc | attggggccc | ataatattcc | taatgcaaat | atgaatgaag | 450 |
| atggcccttc | catgtctgtg | aatttcacct | caccaggctg | cctagaccac | 500 |
| ataatgaaat | ataaaaaaaa | gtgtgtcaag | gccggaagcc | tgtgggatcc | 550 |
| gaacatcact | gcttgtaaga | agaatgagga | gacagtagaa | gtgaacttca | 600 |
| caaccactcc | cctgggaaac | agatacatgg | ctcttatcca | acacagcact | 650 |
| atcatcgggt | tttctcaggt | gtttgagcca | caccagaaga | aacaaacgcg | 700 |
| agcttcagtg | gtgattccag | tgactgggga | tagtgaaggt | gctacggtgc | 750 |
| agctgactcc | atattttcct | acttgtggca | gcgactgcat | ccgacataaa | 800 |
| ggaacagttg | tgctctgccc | acaaacaggc | gtcccttttcc | ctctggataa | 850 |
| caacaaaagc | aagccgggag | gctggctgcc | tctcctcctg | ctgtctctgc | 900 |
| tggtggccac | atgggctg | gtggcaggga | tctatctaat | gtggaggcac | 950 |
| gaaaggatca | gaagacttc | cttttctacc | accacactac | tgcccccat | 1000 |
| taaggttctt | gtggtttacc | catctgaaat | atgtttccat | cacacaattt | 1050 |
| gttacttcac | tgaatttctt | caaaaccatt | gcagaagtga | ggtcatcctt | 1100 |
| gaaaagtggc | agaaaagaa | aatagcgag | atgggtccag | tgcagtggct | 1150 |
| tgccactcaa | aagaaggcag | cagacaaagt | cgtcttcctt | cttttccaatg | 1200 |
| acgtcaacag | tgtgtgcgat | ggtacctgtg | gcaagagcga | gggcagtccc | 1250 |
| agtgagaact | ctcaagacct | cttccccctt | gcctttaacc | ttttctgcag | 1300 |
| tgatctaaga | agccagattc | atctgcacaa | atacgtggtg | gtctactta | 1350 |
| gagagattga | tacaaaagac | gattacaatg | ctctcagtgt | ctgccccaag | 1400 |
| taccacttca | tgaaggatgc | cactgctttc | tgtgcagaac | ttctccatgt | 1450 |
| caagcagcag | gtgtcagcag | gaaaaagatc | acaagcctgc | cacgatggct | 1500 |
| gctgctcctt | gtagcccacc | catgagaagc | aagagacctt | aaaggcttcc | 1550 |
| tatcccacca | attacaggga | aaaaacgtgt | gatgatcctg | aagcttacta | 1600 |

-continued

| | |
|---|---|
| tgcagcctac aaacagcctt agtaattaaa acattttata ccaataaaat | 1650 |
| tttcaaatat tactaactaa tgtagcatta actaacgatt ggaaactaca | 1700 |
| tttacaactt caaagctgtt ttatacatag aaatcaatta cagctttaat | 1750 |
| tgaaaactgt aaccattttg ataatgcaac aataaagcat cttccaaaaa | 1800 |
| aaaaaaaaaa aaaaaaaaaa aaaaaaa | 1827 |

```
<210> SEQ ID NO 2
<211> LENGTH: 2856
<212> TYPE: DNA
<213> ORGANISM: Homo sapiens
<220> FEATURE:
<221> NAME/KEY: prim_transcript
<223> OTHER INFORMATION: cDNA of human Evi27

<400> SEQUENCE: 2
```

| | |
|---|---|
| cggcgatgtc gctcgtgctg ataagcctgg ccgcgctgtg caggagcgcc | 50 |
| gtaccccgag agccgaccgt tcaatgtggc tctgaaactg ggccatctcc | 100 |
| agagtggatg ctacaacatg atctaatccc cggagacttg agggacctcc | 150 |
| gagtagaacc tgttacaact agtgttgcaa caggggacta ttcaattttg | 200 |
| atgaatgtaa gctgggtact ccgggcagat gccagcatcc gcttgttgaa | 250 |
| ggccaccaag atttgtgtga cgggcaaaag caacttccag tcctacagct | 300 |
| gtgtgaggtg caattacaca gaggccttcc agactcagac cagaccctct | 350 |
| ggtggtaaat ggacattttc ctatatcggc ttccctgtag agctgaacac | 400 |
| agtctatttc attggggccc ataatattcc taatgcaaat atgaatgaag | 450 |
| atggcccttc catgtctgtg aatttcacct caccaggctg cctagaccac | 500 |
| ataatgaaat ataaaaaaaa gtgtgtcaag gccggaagcc tgtgggatcc | 550 |
| gaacatcact gcttgtaaga agaatgagga gacagtagaa gtgaacttca | 600 |
| caaccactcc cctgggaaac agatacatgg ctcttatcca acacagcact | 650 |
| atcatcgggt tttctcaggt gtttgagcca accagaagaa acaaacgcg | 700 |
| agcttcagtg gtgattccag tgactgggga tagtgaaggt gctacggtgc | 750 |
| aggtaaagtt cagtgagctg ctctggggag ggaagggaca tagaagactg | 800 |
| ttccatcatt cattgctttt aaggatgagt tctctcttgt caaatgcact | 850 |
| tctgccagca gacaccagtt aagtggcgtt catgggggtt ctttcgctgc | 900 |
| agcctccacc gtgctgaggt caggaggccg acgtggcagt tgtggtccct | 950 |
| tttgcttgta ttaatggctg ctgaccttcc aaagcacttt ttattttcat | 1000 |
| tttctgtcac agacactcag ggatagcagt accattttac ttccgcaagc | 1050 |
| ctttaactgc aagatgaagc tgcaaagggt ttgaaatggg aaggtttgag | 1100 |
| ttccaggcag cgtatgaact ctggagaggg gctgccagtc ctctctgggc | 1150 |
| cgcagcggac ccagctggaa cacaggaagt tggagcagta ggtgctcctt | 1200 |
| cacctctcag tatgtctctt tcaactctag tttttgaagt ggggacacag | 1250 |
| gaagtccagt ggggacacag ccactcccca aagaataagg aacttccatg | 1300 |
| cttcattccc tggcataaaa agtgntcaaa cacaccagag ggggcaggca | 1350 |
| ccagccaggg tatgatgggt actacccttt tctggagaac catagacttc | 1400 |
| ccttactaca gggacttgca tgtcctaaag cactggctga aggaagccaa | 1450 |

-continued

| | |
|---|---|
| gaggatcact gctgctcctt ttttgtagag gaaatgtttg tgtacgtggt | 1500 |
| aagatatgac ctagcccttt taggtaagcg aactggtatg ttagtaacgt | 1550 |
| gtacaaagtt taggttcaga ccccgggagt cttgggcatg tgggtctcgg | 1600 |
| gtcactggtt ttgactttag ggcttttgtta cagatgtgtg accaagggga | 1650 |
| aaatgtgcat gacaacacta gaggtagggg cgaagccaga aagaagggaa | 1700 |
| gttttggctg aagtaggagt cttggtgaga ttttgctgtg atgcatggtg | 1750 |
| tgaactttct gagcctcttg ttttttcctca gctgactcca tattttccta | 1800 |
| cttgtggcag cgactgcatc cgacataaag gaacagttgt gctctgccca | 1850 |
| caaacaggcg tccctttccc tctggataac aacaaaagca agccgggagg | 1900 |
| ctggctgcct ctcctcctgc tgtctctgct ggtggccaca tgggtgctgg | 1950 |
| tggcagggat ctatctaatg tggaggcacg aaaggatcaa gaagacttcc | 2000 |
| ttttctacca ccacactact gcccccatt aaggttcttg tggtttaccc | 2050 |
| atctgaaata tgtttccatc acacaatttg ttacttcact gaatttcttc | 2100 |
| aaaaccattg cagaagtgag gtcatccttg aaaagtggca gaaaaagaaa | 2150 |
| atagcagaga tgggtccagt gcagtggctt gccactcaaa agaaggcagc | 2200 |
| agacaaagtc gtcttccttc tttccaatga cgtcaacagt gtgtgcgatg | 2250 |
| gtacctgtgg caagagcgag ggcagtccca gtgagaactc tcaagacctc | 2300 |
| ttccccttg cctttaacct tttctgcagt gatctaagaa gccagattca | 2350 |
| tctgcacaaa tacgtggtgg tctactttag agagattgat acaaaagacg | 2400 |
| attacaatgc tctcagtgtc tgccccaagt accacttcat gaaggatgcc | 2450 |
| actgctttct gtgcagaact tctccatgtc aagcagcagg tgtcagcagg | 2500 |
| aaaaagatca caagcctgcc acgatggctg ctgctccttg tagcccaccc | 2550 |
| atgagaagca agagacctta aaggcttcct atcccaccaa ttacagggaa | 2600 |
| aaaacgtgtg atgatcctga agcttactat gcagcctaca aacagcctta | 2650 |
| gtaattaaaa cattttatac caataaaatt ttcaaatatt actaactaat | 2700 |
| gtagcattaa ctaacgattg gaaactacat ttacaacttc aaagctgttt | 2750 |
| tatacataga aatcaattac agctttaatt gaaaactgta accattttga | 2800 |
| taatgcaaca ataaagcatc ttccaaaaaa aaaaaaaaa aaaaaaaaa | 2850 |
| aaaaaa | 2856 |

<210> SEQ ID NO 3
<211> LENGTH: 1963
<212> TYPE: DNA
<213> ORGANISM: Unknown
<220> FEATURE:
<221> NAME/KEY: prim_transcript
<223> OTHER INFORMATION: cDNA of mouse Evi27

<400> SEQUENCE: 3

| | |
|---|---|
| gtggccagtg gccgggccat gttgctagtg ttgctgatct tggctgcatc | 50 |
| gtgcaggagc gccctgcctc gagagccgac tattcagtgt ggctctgaga | 100 |
| cagggccatc tccagagtgg atggtccaac acacactcac tccaggagac | 150 |
| ttgagggacc tccaagtgga actcgtcaag acaagtgtgg cagcagagga | 200 |
| gttttcaatt ttgatgaaca taagctggat actccgggca gacgccagca | 250 |

| | |
|---|---|
| tccgcttgtt gaaggccacc aagatctgcg tgagtggcaa aaacaacatg | 300 |
| aattcataca gctgtgtgag gtgcaactac acagaggcct tccaaagcca | 350 |
| gaccagacct tccggcggca aatggacatt ctcctatgta ggcttccctg | 400 |
| tggagctgag cactctctat ctcatcagcg cccataacat ccccaatgct | 450 |
| aatatgaatg aggacagccc ttctttgtct gtgaacttca cctcgccagg | 500 |
| ctgcctaaac cacgtaatga aatataaaaa gcagtgcact gaggcgggaa | 550 |
| gcctgtggga cccagacatc actgcttgta aaagaacga aagatggtt | 600 |
| gaagtgaatt cacaaccaa tccccttgga aacagataca cgattctcat | 650 |
| tcaacgggac acgacattgg ggttttctag agtgctggag aataaactga | 700 |
| tgaggacgtc tgtagccatc ccggtgactg aggagagtga aggtgcggtg | 750 |
| gttcagctga ccccatattt acatacctgc ggcaatgact gcatccgacg | 800 |
| cgaagggaca gttgtgcttt gctcagagac aagtgctccc atccctccag | 850 |
| atgacaacag acgcatgctg ggaggctggc tgcctctctt cctggtgctg | 900 |
| ctggtggctg tgtgggtgct ggcagctggg atctacctaa cttggaggca | 950 |
| aggaaggagc acgaagacgt cctttcctat ttccaccatg ctcctgcccc | 1000 |
| tcattaaggt cctggtggtt tatccttctg agatatgttt ccatcacacc | 1050 |
| gtctgtcgct tcactgactt tcttcaaaac tactgcagaa gtgaggtcat | 1100 |
| ccttgaaaaa tggcagaaaa agaaaatcgc cgagatgggg ccggtacagt | 1150 |
| ggctgaccac tcagaagcaa gcggcagata aagtggtctt ccttcttccc | 1200 |
| agtgacgtcc cgacccttg tgacagtgcc tgtggccaca atgagggcag | 1250 |
| cgccagggag aactctcagg atctgttccc tcttgccttt aacctctttt | 1300 |
| gtagtgattt cagcagccag acgcatctgc acaaataccct ggtggtctat | 1350 |
| cttggggag cagacctcaa aggcgactat aatgccctga gtgtctgccc | 1400 |
| ccaatatcat ctcatgaagg acgccacagc tttccacaca gaacttctca | 1450 |
| aggctacgca gagcatgtca gtgaagaaac gctcacaagc ctgccatgat | 1500 |
| agctgttcac ccttgtagtc cacccggggg aatagagact ctgaagcctt | 1550 |
| cctactctcc cttccagtga caaatgctgt gtgacgactc tgaaatgtgt | 1600 |
| gggagaggct gtgtggaggt agtgctatgt acaaacttgc tttaaaactg | 1650 |
| gagtttgcaa agtcaacctg agcatacacg cctgaggcta gtcattggct | 1700 |
| ggatttatga agacaacaca gttacagaca ataatgagtg ggacctacat | 1750 |
| ttgggatata cccaaagctg ggtaatgatt atcactgaga accacgcact | 1800 |
| ctggccatga agtaatacgg cacttccctg tcaggctgtc tgtcaggttg | 1850 |
| ggtctgtctt gcactgccca tgctctatgc tgcacgtaga ccgttttgta | 1900 |
| acattttaat ctgttaatga ataatccgtt tgggaagctc tcaaaaaaaa | 1950 |
| aaaaaaaaaa aaa | 1963 |

```
<210> SEQ ID NO 4
<211> LENGTH: 2589
<212> TYPE: DNA
<213> ORGANISM: Unknown
<220> FEATURE:
<221> NAME/KEY: prim_transcript
<223> OTHER INFORMATION: cDNA of mouse Evi27
```

<400> SEQUENCE: 4

```
gtggccagtg gccgggccat gttgctagtg ttgctgatct tggctgcatc          50
gtgcaggagc gccctgcctc gagagccgac tattcagtgt ggctctgaga         100
cagggccatc tccagagtgg atggtccaac acacactcac tccaggagac         150
ttgagggacc tccaagtgga actcgtcaag acaagtgtgg cagcagagga         200
gttttcaatt ttgatgaaca taagctggat actccgggca gacgccagca         250
tccgcttgtt gaaggccacc aagatctgcg tgagtggcaa aaacaacatg         300
aattcataca gctgtgtgag gtgcaactac acagaggcct ccaaagcca          350 gaccagacct tccggcggca atggacatt ctcctatgta ggcttccctg          400
tggagctgag cactctctat ctcatcagcg cccataacat ccccaatgct         450
aatatgaatg aggacagccc ttctttgtct gtgaacttca cctcgccagg         500
gtgcactcgt gaaaacacag aagtaacgtc cggtgtattt ccagcagcta         550
aacaccaggc tctccggatt tcagctcctt tcccattaca atttcctcct         600
gggccagagg actcagtcat tctgccaccc cagcctctgg cgtcgctttt         650
tcatgacttt gtcaaactta cctagcttgt ttccattctg aaattgtctg         700
atgcttgctt cgtatgtaag ccggggatat gaggtttggg tatgaatccc         750
acagagggca ctgaattctt ctcactatgg cctatctggg ctgtgtgaca         800
ttgttggtga gggtcgtgcc tactaggcat ctgggtatct accacctgga         850
gcttcatgtc tggaagaggc agaacctata tgtattgtca gctctcactt         900
ttgtttccgt gtcacctcct ggagactgtt tttgataaag gttgtactta         950
aaggagatta cttaaagctt ccgtggaaga atggtttcct atttagatct        1000
gttgtctctc atatctgaag taagtgtgtg tgtgtgtgtt ttgtgtgtgt        1050
gtgtgtgtgt gtgtgtgtac tgggcaaagg gttataccctt tactcaaatg       1100 taacaacttt cattcacatt cccaggctgc ctaaaccacg taatgaaata        1150
taaaaagcag tgcactgagg cgggaagcct gtgggaccca gacatcactg        1200
cttgtaaaaa gaacgagaag atggttgaag tgaatttcac aaccaatccc        1250
cttggaaaca gatacacgat tctcattcaa cgggacacga cattgggggtt       1300 ttctagagtg ctggagaata aactgatgag gacgtctgta gccatcccgg        1350
tgactgagga gagtgaaggt gcggtggttc agctgacccc atatttacat        1400
acctgcggca atgactgcat ccgacgcgaa gggacagttg tgctttgctc        1450
agagacaagt gctcccatcc ctccagatga caacagacgc atgctgggag        1500
gctggctgcc tctcttcctg gtgctgctgg tggctgtgtg ggtgctggca        1550
gctgggatct acctaacttg gaggcaagga aggagcacga agacgtcctt        1600
tcctatttcc accatgctcc tgcccctcat taaggtcctg gtggtttatc        1650
cttctgagat atgtttccat cacaccgtct gtcgcttcac tgactttctt        1700
caaaactact gcagaagtga ggtcatcctt gaaaaatggc agaaaaagaa        1750
aatcgccgag atgggccgg tacagtggct gaccactcag aagcaagcgg         1800
cagataaagt ggtcttcctt cttcccagtg acgtcccgac cctttgtgac        1850
agtgcctgtg ccacaatga gggcagcgcc agggagaact ctcaggatct         1900
gttccctctt gcctttaacc tcttttgtag tgatttcagc agccagacgc        1950
```

-continued

| | |
|---|---|
| atctgcacaa atacctggtg gtctatcttg ggggagcaga cctcaaaggc | 2000 |
| gactataatg ccctgagtgt ctgccccaa tatcatctca tgaaggacgc | 2050 |
| cacagctttc cacacagaac ttctcaaggc tacgcagagc atgtcagtga | 2100 |
| agaaacgctc acaagcctgc catgatagct gttcaccctt gtagtccacc | 2150 |
| cggggggaata gagactctga agccttccta ctctcccttc cagtgacaaa | 2200 |
| tgctgtgtga cgactctgaa atgtgtggga gaggctgtgt ggaggtagtg | 2250 |
| ctatgtacaa acttgcttta aaactggagt ttgcaaagtc aacctgagca | 2300 |
| tacacgcctg aggctagtca ttggctggat ttatgaagac aacacagtta | 2350 |
| cagacaataa tgagtgggac ctacatttgg gatatacca aagctgggta | 2400 |
| atgattatca ctgagaacca cgcactctgg ccatgaagta atacggcact | 2450 |
| tccctgtcag gctgtctgtc aggttgggtc tgtcttgcac tgcccatgct | 2500 |
| ctatgctgca cgtagaccgt tttgtaacat tttaatctgt taatgaataa | 2550 |
| tccgtttggg aagctctcaa aaaaaaaaaa aaaaaaaa | 2589 |

<210> SEQ ID NO 5
<211> LENGTH: 502
<212> TYPE: PRT
<213> ORGANISM: Homo sapiens
<220> FEATURE:
<221> NAME/KEY: peptide
<223> OTHER INFORMATION: Human Evi27 protein

<400> SEQUENCE: 5

```
Met Ser Leu Val Leu Ile Ser Leu Ala Ala Leu Cys Arg Ser Ala
            5                  10                  15

Val Pro Arg Glu Pro Thr Val Gln Cys Gly Ser Glu Thr Gly Pro
            20                  25                  30

Ser Pro Glu Trp Met Leu Gln His Asp Leu Ile Pro Gly Asp Leu
            35                  40                  45

Arg Asp Leu Arg Val Glu Pro Val Thr Thr Ser Val Ala Thr Gly
            50                  55                  60

Asp Tyr Ser Ile Leu Met Asn Val Ser Trp Val Leu Arg Ala Asp
            65                  70                  75

Ala Ser Ile Arg Leu Leu Lys Ala Thr Lys Ile Cys Val Thr Gly
            80                  85                  90

Lys Ser Asn Phe Gln Ser Tyr Ser Cys Val Arg Cys Asn Tyr Thr
            95                  100                 105

Glu Ala Phe Gln Thr Gln Thr Arg Pro Ser Gly Gly Lys Trp Thr
            110                 115                 120

Phe Ser Tyr Ile Gly Phe Pro Val Glu Leu Asn Thr Val Tyr Phe
            125                 130                 135

Ile Gly Ala His Asn Ile Pro Asn Ala Asn Met Asn Glu Asp Gly
            140                 145                 150

Pro Ser Met Ser Val Asn Phe Thr Ser Pro Gly Cys Leu Asp His
            155                 160                 165

Ile Met Lys Tyr Lys Lys Lys Cys Val Lys Ala Gly Ser Leu Trp
            170                 175                 180

Asp Pro Asn Ile Thr Ala Cys Lys Lys Asn Glu Glu Thr Val Glu
            185                 190                 195

Val Asn Phe Thr Thr Thr Pro Leu Gly Asn Arg Tyr Met Ala Leu
            200                 205                 210
```

Ile Gln His Ser Thr Ile Ile Gly Phe Ser Gln Val Phe Glu Pro
                215                 220                 225

His Gln Lys Lys Gln Thr Arg Ala Ser Val Ile Pro Val Thr
                230                 235                 240

Gly Asp Ser Glu Gly Ala Thr Val Gln Leu Thr Pro Tyr Phe Pro
                245                 250                 255

Thr Cys Gly Ser Asp Cys Ile Arg His Lys Gly Thr Val Val Leu
                260                 265                 270

Cys Pro Gln Thr Gly Val Pro Phe Pro Leu Asp Asn Asn Lys Ser
                275                 280                 285

Lys Pro Gly Gly Trp Leu Pro Leu Leu Leu Ser Leu Leu Val
                290                 295                 300

Ala Thr Trp Val Leu Val Ala Gly Ile Tyr Leu Met Trp Arg His
                305                 310                 315

Glu Arg Ile Lys Lys Thr Ser Phe Ser Thr Thr Thr Leu Leu Pro
                320                 325                 330

Pro Ile Lys Val Leu Val Val Tyr Pro Ser Glu Ile Cys Phe His
                335                 340                 345

His Thr Ile Cys Tyr Phe Thr Glu Phe Leu Gln Asn His Cys Arg
                350                 355                 360

Ser Glu Val Ile Leu Glu Lys Trp Gln Lys Lys Ile Ala Glu
                365                 370                 375

Met Gly Pro Val Gln Trp Leu Ala Thr Gln Lys Lys Ala Ala Asp
                380                 385                 390

Lys Val Val Phe Leu Leu Ser Asn Asp Val Asn Ser Val Cys Asp
                395                 400                 405

Gly Thr Cys Gly Lys Ser Glu Gly Ser Pro Ser Glu Asn Ser Gln
                410                 415                 420

Asp Leu Phe Pro Leu Ala Phe Asn Leu Phe Cys Ser Asp Leu Arg
                425                 430                 435

Ser Gln Ile His Leu His Lys Tyr Val Val Tyr Phe Arg Glu
                440                 445                 450

Ile Asp Thr Lys Asp Asp Tyr Asn Ala Leu Ser Val Cys Pro Lys
                455                 460                 465

Tyr His Phe Met Lys Asp Ala Thr Ala Phe Cys Ala Glu Leu Leu
                470                 475                 480

His Val Lys Gln Gln Val Ser Ala Gly Lys Arg Ser Gln Ala Cys
                485                 490                 495

His Asp Gly Cys Cys Ser Leu
                500

<210> SEQ ID NO 6
<211> LENGTH: 288
<212> TYPE: PRT
<213> ORGANISM: Homo sapiens
<220> FEATURE:
<221> NAME/KEY: peptide
<223> OTHER INFORMATION: Human Evi27 protein

<400> SEQUENCE: 6

Met Ser Leu Val Leu Ile Ser Leu Ala Ala Leu Cys Arg Ser Ala
                5                   10                  15

Val Pro Arg Glu Pro Thr Val Gln Cys Gly Ser Glu Thr Gly Pro
                20                  25                  30

Ser Pro Glu Trp Met Leu Gln His Asp Leu Ile Pro Gly Asp Leu

```
                    35                  40                  45
Arg Asp Leu Arg Val Glu Pro Val Thr Thr Ser Val Ala Thr Gly
                50                  55                  60
Asp Tyr Ser Ile Leu Met Asn Val Ser Trp Val Leu Arg Ala Asp
            65                  70                  75
Ala Ser Ile Arg Leu Leu Lys Ala Thr Lys Ile Cys Val Thr Gly
        80                  85                  90
Lys Ser Asn Phe Gln Ser Tyr Ser Cys Val Arg Cys Asn Tyr Thr
    95                 100                 105
Glu Ala Phe Gln Thr Gln Thr Arg Pro Ser Gly Gly Lys Trp Thr
            110                 115                 120
Phe Ser Tyr Ile Gly Phe Pro Val Glu Leu Asn Thr Val Tyr Phe
            125                 130                 135
Ile Gly Ala His Asn Ile Pro Asn Ala Asn Met Asn Glu Asp Gly
            140                 145                 150
Pro Ser Met Ser Val Asn Phe Thr Ser Pro Gly Cys Leu Asp His
            155                 160                 165
Ile Met Lys Tyr Lys Lys Cys Val Lys Ala Gly Ser Leu Trp
            170                 175                 180
Asp Pro Asn Ile Thr Ala Cys Lys Lys Asn Glu Glu Thr Val Glu
            185                 190                 195
Val Asn Phe Thr Thr Thr Pro Leu Gly Asn Arg Tyr Met Ala Leu
            200                 205                 210
Ile Gln His Ser Thr Ile Ile Gly Phe Ser Gln Val Phe Glu Pro
            215                 220                 225
His Gln Lys Lys Gln Thr Arg Ala Ser Val Val Ile Pro Val Thr
            230                 235                 240
Gly Asp Ser Glu Gly Ala Thr Val Gln Val Lys Phe Ser Glu Leu
            245                 250                 255
Leu Trp Gly Gly Lys Gly His Arg Arg Leu Phe His His Ser Leu
            260                 265                 270
Leu Leu Arg Met Ser Ser Leu Leu Ser Asn Ala Leu Leu Pro Ala
            275                 280                 285
Asp Thr Ser
        288

<210> SEQ ID NO 7
<211> LENGTH: 499
<212> TYPE: PRT
<213> ORGANISM: Unknown
<220> FEATURE:
<221> NAME/KEY: peptide
<223> OTHER INFORMATION: Mouse Evi27 protein

<400> SEQUENCE: 7

Met Leu Leu Val Leu Leu Ile Leu Ala Ala Ser Cys Arg Ser Ala
                 5                  10                  15
Leu Pro Arg Glu Pro Thr Ile Gln Cys Gly Ser Glu Thr Gly Pro
                20                  25                  30
Ser Pro Glu Trp Met Val Gln His Thr Leu Thr Pro Gly Asp Leu
            35                  40                  45
Arg Asp Leu Gln Val Glu Leu Val Lys Thr Ser Val Ala Ala Glu
        50                  55                  60
Glu Phe Ser Ile Leu Met Asn Ile Ser Trp Ile Leu Arg Ala Asp
    65                  70                  75
```

-continued

```
Ala Ser Ile Arg Leu Leu Lys Ala Thr Lys Ile Cys Val Ser Gly
             80                  85                  90

Lys Asn Asn Met Asn Ser Tyr Ser Cys Val Arg Cys Asn Tyr Thr
             95                 100                 105

Glu Ala Phe Gln Ser Gln Thr Arg Pro Ser Gly Gly Lys Trp Thr
            110                 115                 120

Phe Ser Tyr Val Gly Phe Pro Val Glu Leu Ser Thr Leu Tyr Leu
            125                 130                 135

Ile Ser Ala His Asn Ile Pro Asn Ala Asn Met Asn Glu Asp Ser
            140                 145                 150

Pro Ser Leu Ser Val Asn Phe Thr Ser Pro Gly Cys Leu Asn His
            155                 160                 165

Val Met Lys Tyr Lys Lys Gln Cys Thr Glu Ala Gly Ser Leu Trp
            170                 175                 180

Asp Pro Asp Ile Thr Ala Cys Lys Lys Asn Glu Lys Met Val Glu
            185                 190                 195

Val Asn Phe Thr Thr Asn Pro Leu Gly Asn Arg Tyr Thr Ile Leu
            200                 205                 210

Ile Gln Arg Asp Thr Thr Leu Gly Phe Ser Arg Val Leu Glu Asn
            215                 220                 225

Lys Leu Met Arg Thr Ser Val Ala Ile Pro Val Thr Glu Glu Ser
            230                 235                 240

Glu Gly Ala Val Val Gln Leu Thr Pro Tyr Leu His Thr Cys Gly
            245                 250                 255

Asn Asp Cys Ile Arg Arg Glu Gly Thr Val Val Leu Cys Ser Glu
            260                 265                 270

Thr Ser Ala Pro Ile Pro Pro Asp Asp Asn Arg Arg Met Leu Gly
            275                 280                 285

Gly Trp Leu Pro Leu Phe Leu Val Leu Val Ala Val Trp Val
            290                 295                 300

Leu Ala Ala Gly Ile Tyr Leu Thr Trp Arg Gln Gly Arg Ser Thr
            305                 310                 315

Lys Thr Ser Phe Pro Ile Ser Thr Met Leu Leu Pro Leu Ile Lys
            320                 325                 330

Val Leu Val Val Tyr Pro Ser Glu Ile Cys Phe His His Thr Val
            335                 340                 345

Cys Arg Phe Thr Asp Phe Leu Gln Asn Tyr Cys Arg Ser Glu Val
            350                 355                 360

Ile Leu Glu Lys Trp Gln Lys Lys Ile Ala Glu Met Gly Pro
            365                 370                 375

Val Gln Trp Leu Thr Thr Gln Lys Gln Ala Ala Asp Lys Val Val
            380                 385                 390

Phe Leu Leu Pro Ser Asp Val Pro Thr Leu Cys Asp Ser Ala Cys
            395                 400                 405

Gly His Asn Glu Gly Ser Ala Arg Glu Asn Ser Gln Asp Leu Phe
            410                 415                 420

Pro Leu Ala Phe Asn Leu Phe Cys Ser Asp Phe Ser Ser Gln Thr
            425                 430                 435

His Leu His Lys Tyr Leu Val Val Tyr Leu Gly Gly Ala Asp Leu
            440                 445                 450

Lys Gly Asp Tyr Asn Ala Leu Ser Val Cys Pro Gln Tyr His Leu
            455                 460                 465

Met Lys Asp Ala Thr Ala Phe His Thr Glu Leu Leu Lys Ala Thr
```

470                 475                 480
Gln Ser Met Ser Val Lys Lys Arg Ser Gln Ala Cys His Asp Ser
                485                 490                 495

Cys Ser Pro Leu
            499

<210> SEQ ID NO 8
<211> LENGTH: 289
<212> TYPE: PRT
<213> ORGANISM: Unknown
<220> FEATURE:
<221> NAME/KEY: peptide
<223> OTHER INFORMATION: Mouse Evi27 protein

<400> SEQUENCE: 8

Met Leu Leu Val Leu Leu Ile Leu Ala Ala Ser Cys Arg Ser Ala
                 5                  10                  15

Leu Pro Arg Glu Pro Thr Ile Gln Cys Gly Ser Glu Thr Gly Pro
                20                  25                  30

Ser Pro Glu Trp Met Val Gln His Thr Leu Thr Pro Gly Asp Leu
                35                  40                  45

Arg Asp Leu Gln Val Glu Leu Val Lys Thr Ser Val Ala Ala Glu
                50                  55                  60

Glu Phe Ser Ile Leu Met Asn Ile Ser Trp Ile Leu Arg Ala Asp
                65                  70                  75

Ala Ser Ile Arg Leu Leu Lys Ala Thr Lys Ile Cys Val Ser Gly
                80                  85                  90

Lys Asn Asn Met Asn Ser Tyr Ser Cys Val Arg Cys Asn Tyr Thr
                95                 100                 105

Glu Ala Phe Gln Ser Gln Thr Arg Pro Ser Gly Gly Lys Trp Thr
               110                 115                 120

Phe Ser Tyr Val Gly Phe Pro Val Glu Leu Ser Thr Leu Tyr Leu
               125                 130                 135

Ile Ser Ala His Asn Ile Pro Asn Ala Asn Met Asn Glu Asp Ser
               140                 145                 150

Pro Ser Leu Ser Val Asn Phe Thr Ser Pro Gly Cys Leu Asn His
               155                 160                 165

Val Met Lys Tyr Lys Lys Gln Cys Thr Glu Ala Gly Ser Leu Trp
               170                 175                 180

Asp Pro Asp Ile Thr Ala Cys Lys Lys Asn Glu Lys Met Val Glu
               185                 190                 195

Val Asn Phe Thr Thr Asn Pro Leu Gly Asn Arg Tyr Thr Ile Leu
               200                 205                 210

Ile Gln Arg Asp Thr Thr Leu Gly Phe Ser Arg Val Leu Glu Asn
               215                 220                 225

Lys Leu Met Arg Thr Ser Val Ala Ile Pro Val Thr Glu Glu Ser
               230                 235                 240

Glu Gly Ala Val Val Gln Leu Thr Pro Tyr Leu His Thr Cys Gly
               245                 250                 255

Asn Asp Cys Ile Arg Arg Glu Gly Thr Val Val Leu Cys Ser Glu
               260                 265                 270

Thr Ser Ala Pro Ile Pro Pro Asp Asp Asn Arg Arg Met Leu Gly
               275                 280                 285

Gly Trp Leu Pro
            289

<210> SEQ ID NO 9
<211> LENGTH: 866
<212> TYPE: PRT
<213> ORGANISM: Unknown
<220> FEATURE:
<221> NAME/KEY: peptide
<223> OTHER INFORMATION: IL-17 receptor protein

<400> SEQUENCE: 9

```
Met Gly Ala Ala Arg Ser Pro Pro Ser Ala Val Pro Gly Pro Leu
                5                  10                  15

Leu Gly Leu Leu Leu Leu Leu Gly Val Leu Ala Pro Gly Gly
            20                  25                  30

Ala Ser Leu Arg Leu Leu Asp His Arg Ala Leu Val Cys Ser Gln
            35                  40                  45

Pro Gly Leu Asn Cys Thr Val Lys Asn Ser Thr Cys Leu Asp Asp
            50                  55                  60

Ser Trp Ile His Pro Arg Asn Leu Thr Pro Ser Ser Pro Lys Asp
            65                  70                  75

Leu Gln Ile Gln Leu His Phe Ala His Thr Gln Gln Gly Asp Leu
            80                  85                  90

Phe Pro Val Ala His Ile Glu Trp Thr Leu Gln Thr Asp Ala Ser
            95                  100                 105

Ile Leu Tyr Leu Glu Gly Ala Glu Leu Ser Val Leu Gln Leu Asn
            110                 115                 120

Thr Asn Glu Arg Leu Cys Val Arg Phe Glu Phe Leu Ser Lys Leu
            125                 130                 135

Arg His His His Arg Arg Trp Arg Phe Thr Phe Ser His Phe Val
            140                 145                 150

Val Asp Pro Asp Gln Glu Tyr Glu Val Thr Val His His Leu Pro
            155                 160                 165

Lys Pro Ile Pro Asp Gly Asp Pro Asn His Gln Ser Lys Asn Phe
            170                 175                 180

Leu Val Pro Asp Cys Glu His Ala Arg Met Lys Val Thr Thr Pro
            185                 190                 195

Cys Met Ser Ser Gly Ser Leu Trp Asp Pro Asn Ile Thr Val Glu
            200                 205                 210

Thr Leu Glu Ala His Gln Leu Arg Val Ser Phe Thr Leu Trp Asn
            215                 220                 225

Glu Ser Thr His Tyr Gln Ile Leu Leu Thr Ser Phe Pro His Met
            230                 235                 240

Glu Asn His Ser Cys Phe Glu His Met His His Ile Pro Ala Pro
            245                 250                 255

Arg Pro Glu Glu Phe His Gln Arg Ser Asn Val Thr Leu Thr Leu
            260                 265                 270

Arg Asn Leu Lys Gly Cys Cys Arg His Gln Val Gln Ile Gln Pro
            275                 280                 285

Phe Phe Ser Ser Cys Leu Asn Asp Cys Leu Arg His Ser Ala Thr
            290                 295                 300

Val Ser Cys Pro Glu Met Pro Asp Thr Pro Glu Pro Ile Pro Asp
            305                 310                 315

Tyr Met Pro Leu Trp Val Tyr Trp Phe Ile Thr Gly Ile Ser Ile
            320                 325                 330

Leu Leu Val Gly Ser Val Ile Leu Leu Ile Val Cys Met Thr Trp
            335                 340                 345
```

-continued

```
Arg Leu Ala Gly Pro Gly Ser Glu Lys Tyr Ser Asp Asp Thr Lys
                350                 355                 360
Tyr Thr Asp Gly Leu Pro Ala Ala Asp Leu Ile Pro Pro Pro Leu
                365                 370                 375
Lys Pro Arg Lys Val Trp Ile Ile Tyr Ser Ala Asp His Pro Leu
                380                 385                 390
Tyr Val Asp Val Val Leu Lys Phe Ala Gln Phe Leu Leu Thr Ala
                395                 400                 405
Cys Gly Thr Glu Val Ala Leu Asp Leu Leu Glu Glu Gln Ala Ile
                410                 415                 420
Ser Glu Ala Gly Val Met Thr Trp Val Gly Arg Gln Lys Gln Glu
                425                 430                 435
Met Val Glu Ser Asn Ser Lys Ile Ile Val Leu Cys Ser Arg Gly
                440                 445                 450
Thr Arg Ala Lys Trp Gln Ala Leu Leu Gly Arg Gly Ala Pro Val
                455                 460                 465
Arg Leu Arg Cys Asp His Gly Lys Pro Val Gly Asp Leu Phe Thr
                470                 475                 480
Ala Ala Met Asn Met Ile Leu Pro Asp Phe Lys Arg Pro Ala Cys
                485                 490                 495
Phe Gly Thr Tyr Val Val Cys Tyr Phe Ser Glu Val Ser Cys Asp
                500                 505                 510
Gly Asp Val Pro Asp Leu Phe Gly Ala Ala Pro Arg Tyr Pro Leu
                515                 520                 525
Met Asp Arg Phe Glu Glu Val Tyr Phe Arg Ile Gln Asp Leu Glu
                530                 535                 540
Met Phe Gln Pro Gly Arg Met His Arg Val Gly Glu Leu Ser Gly
                545                 550                 555
Asp Asn Tyr Leu Arg Ser Pro Gly Gly Arg Gln Leu Arg Ala Ala
                560                 565                 570
Leu Asp Arg Phe Arg Asp Trp Gln Val Arg Cys Pro Asp Trp Phe
                575                 580                 585
Glu Cys Glu Asn Leu Tyr Ser Ala Asp Asp Gln Asp Ala Pro Ser
                590                 595                 600
Leu Asp Glu Glu Val Phe Glu Glu Pro Leu Leu Pro Pro Gly Thr
                605                 610                 615
Gly Ile Val Lys Arg Ala Pro Leu Val Arg Glu Pro Gly Ser Gln
                620                 625                 630
Ala Cys Leu Ala Ile Asp Pro Leu Val Gly Glu Glu Gly Gly Ala
                635                 640                 645
Ala Val Ala Lys Leu Glu Pro His Leu Gln Pro Arg Gly Gln Pro
                650                 655                 660
Ala Pro Gln Pro Leu His Thr Leu Val Leu Ala Ala Glu Glu Gly
                665                 670                 675
Ala Leu Val Ala Ala Val Glu Pro Gly Pro Leu Ala Asp Gly Ala
                680                 685                 690
Ala Val Arg Leu Ala Leu Ala Gly Glu Gly Glu Ala Cys Pro Leu
                695                 700                 705
Leu Gly Ser Pro Gly Ala Gly Arg Asn Ser Val Leu Phe Leu Pro
                710                 715                 720
Val Asp Pro Glu Asp Ser Pro Leu Gly Ser Ser Thr Pro Met Ala
                725                 730                 735
```

```
-continued

Ser Pro Asp Leu Leu Pro Glu Asp Val Arg Glu His Leu Glu Gly
                740                 745                 750

Leu Met Leu Ser Leu Phe Glu Gln Ser Leu Ser Cys Gln Ala Gln
                755                 760                 765

Gly Gly Cys Ser Arg Pro Ala Met Val Leu Thr Asp Pro His Thr
                770                 775                 780

Pro Tyr Glu Glu Glu Arg Gln Ser Val Gln Ser Asp Gln Gly
                785                 790                 795

Tyr Ile Ser Arg Ser Ser Pro Gln Pro Pro Glu Gly Leu Thr Glu
                800                 805                 810

Met Glu Glu Glu Glu Glu Glu Gln Asp Pro Gly Lys Pro Ala
                815                 820                 825

Leu Pro Leu Ser Pro Glu Asp Leu Glu Ser Leu Pro Ser Leu Gln
                830                 835                 840

Arg Gln Leu Leu Phe Arg Gln Leu Gln Lys Asn Ser Gly Trp Asp
                845                 850                 855

Thr Met Gly Ser Glu Ser Glu Gly Pro Ser Ala
                860                 865
```